(12) United States Patent
Brown

(10) Patent No.: US 8,278,498 B2
(45) Date of Patent: Oct. 2, 2012

(54) METHOD FOR PRODUCING IMMORTALISED ANTIBODIES-SECRETING CELLS

(75) Inventor: Jason Peter Brown, Cambridge (GB)

(73) Assignee: Granta Biotechnology Limited, Cambridge (GB)

( * ) Notice: Subject to any disclaimer, the term of this patent is extended or adjusted under 35 U.S.C. 154(b) by 1002 days.

(21) Appl. No.: 10/511,515

(22) PCT Filed: Apr. 16, 2003

(86) PCT No.: PCT/GB03/01650
§ 371 (c)(1),
(2), (4) Date: Dec. 19, 2005

(87) PCT Pub. No.: WO03/089630
PCT Pub. Date: Oct. 30, 2003

(65) Prior Publication Data
US 2007/0130628 A1  Jun. 7, 2007

(30) Foreign Application Priority Data
Apr. 17, 2002 (GB) .................................. 0208819.3

(51) Int. Cl.
C12P 21/00 (2006.01)
C12N 5/06 (2006.01)
(52) U.S. Cl. ..................... 800/6; 435/326; 800/4; 800/5
(58) Field of Classification Search .......................... None
See application file for complete search history.

(56) References Cited

U.S. PATENT DOCUMENTS

| | | | |
|---|---|---|---|
| 4,833,080 A | 5/1989 | Brent et al. | |
| 5,514,578 A | 5/1996 | Hogness et al. | |
| 5,688,692 A | 11/1997 | Jat et al. | |
| 5,798,230 A | 8/1998 | Bornkamm et al. | |
| 5,866,759 A * | 2/1999 | Jat et al. ........................... | 800/18 |
| 5,874,299 A | 2/1999 | Lonberg et al. | |
| 5,877,397 A | 3/1999 | Lonberg et al. | |
| 6,114,598 A | 9/2000 | Kucherlapati et al. | |
| 6,150,584 A | 11/2000 | Kucherlapati et al. | |
| 6,194,205 B1 | 2/2001 | Staege et al. | |
| 6,207,418 B1 | 3/2001 | Hori et al. | |
| 6,245,531 B1 | 6/2001 | Hogness et al. | |
| 6,258,603 B1 | 7/2001 | Carlson et al. | |
| 6,300,129 B1 | 10/2001 | Lonberg et al. | |
| 6,358,737 B1 | 3/2002 | Bonewald et al. | |

FOREIGN PATENT DOCUMENTS

| | | |
|---|---|---|
| JP | 10-506266 | 6/1998 |
| WO | WO96/02646 | 2/1996 |

OTHER PUBLICATIONS

Zaccolo et al. Int J Clin Res 1993;23:192-8.*
Yu et al. Oncogene Mar. 2002;21:1922-7.*
Felsher et al. Mol Cell 1999;4:199-207.*
Irsch et al. Immunotechnol 1995;1:115-25.*
No et al. PNAS 1996;93:3346-51.*
Yokoyama Curr Protoc Immunol 2001;Appendix 3G.*
Marinkovic et al. Int. J Cancer 2004;110:336-42.*
Benjamin et al. J Immunol 1982;129:1336-42.*
Shammah et al. J Immunol Methods 1993;160:19-25.*
Search Report from EP03722744.4, May 22, 2006.
Kumar, A., et al., 1999, "Bcl2 and v-abl Oncogenes Cooperate to Immortalize Murine B Cells That Secrete Antigen Specific Antibodies," *Immunology Letters* 65:153-159.
International Patent Application Publication No. WO99/45962, Sep. 16, 1999.
Albanese et al. (2002) Seminars in Cell and Developmental Biology 13:129-441.
Jaisser (2000) J. Am. Soc. Nephrol. 11:S95-S100.
Knott et al. (1996) Hybridoma 15:365-371.
Pajic et al. (2001) Int. J. Cancer 93:810-816.
Pavirani et al. (1989) Bio/Technology 7:1049-4054.
Ryding et al, (2001) Journal of Endocrinology 171:1-4.
Theisen et al. (1995) Strategies in Transgenic Animal Science, 311-324, American Society for Microbiology Books Division, Washington, DC.
Weissinger et al. (1991) Proc. Natl. Acad. Sci. USA 88:8735-8739.
Adams, J.M, and Cory, S. (1985) Myc oncogene activation in B and T lymphoid tumours. Proc. R. Soc. Lond. Biol. Sci. 226(1242), 59-72, Abstract.
Adams, J.M., Harris, A.W., Strasser, A., Ogilvy, S. and Cory, S. (1999) Transgenic models of lymphoid neoplasia and development of a pan-hematopoietic vector. Oncogene 18(38), 5268-5277.
Albanese, C., Rentens, A.T., Bouzahzah, B., Fu, M., D'Amico, M., Link, T., Nicholson, R., Dephino, R.A. and Pestell, R.G. (2000) Sustained mammary gland-directed, ponasterone A-inducible expression in transgenic mice. FASEB J. 14, 877884.
Allen, K.L. Reyes, R., Demmler, K., Mercer, J.F., Williamson, R. and Whitehead, R.H. (2000) Conditionally immortalized mouse hepatocytes for use in liver gene therapy. J Gastroenterol. Hepatol. 15(11), 1325-1332.
Allman, D.M., Ferguson, S.E., Lentz. V.M. and Cancro, M.P. (1993) Peripheral B cell maturation. II. Heat-stable antigen(hi) splenic B cells are an immature developmental intermediate in the production of long-lived marrow-derived B cells. J Immunol, 151(9), 4431-4444.
Amara, J.F., Clackson, T., Rivera, V.M., Guo, T., Keenan, T., Natesan, S., Pollock, R., Yang, W., Courage, N.L., Holt, D.A. and Gilman, M. (1997) A versatile synthetic dimerzer for the regulation of protein-protein interactions. Proc. Natl. Acad. Sci. USA 94, 10618-10623.
Atom, V. and Iversen (2000) Antisense oligonucleotides targeted to the p53 gene modulate liver regeneration in vivo. Drug Met. Disp. 28(2). 133-138.

(Continued)

*Primary Examiner* — Q. Janice Li
(74) *Attorney, Agent, or Firm* — Shelly Guest Cermak; Cermak Nakajima LLP

(57) ABSTRACT

A method for producing immortalized antibody-secreting cells, comprising: (a) providing a transgenic animal having antibody-secreting cells capable of expressing one or more transgenes, wherein the antibody-secreting cells are in a non-immortalized state in the absence of a stimulus and are capable of changing to an immortalized state by means of the transgene or transgenes upon exposure of the cells to the stimulus; (b) extracting the antibody-secreting cells from the animal; and (c) exposing the antibody-secreting cells to the stimulus, thereby immortalizing the antibody secreting cells by means of the transgene or transgenes.

32 Claims, No Drawings

OTHER PUBLICATIONS

Barrald, K.F. and Wessells, N.K. (1984) Differential antigen adhesivity used to select spleen cells for the production of monoclonal antibodies to embryonic neurons. J. Immunol. Methods 73(1), 1-15.

Bennick, A., Gron, B. and Brosstad, F. (1991) Hybridomas can successfully be prepared from frozen/thawn spleen cells. Hybridoma 10(6), 761-765. Abstract.

Boerner, P., Lafond, R., Lu, W.Z., Brams, P. and Royston, I. (1991) Production of antigen-specific human monoclonal antibodies from in vitro-primed human spenocytes. J. Immunol. 147(1), 86-95.

Cannell, E.J., Farrell, P.J. and Sinclair, A.J. (1996) Epstein-Barr virus exploits the normal cell pathway to regulate Rb activity during the immortalisation of primary B-cells. Oncogene 13(7), 1413-1421.

Carnero, A., Hudson, J.D., Hannon, G.J. and Beach, D.H. (2000) Loss-of-function genetics in mammalian cells: the p53 tumor suppressor model. Nucleic Acids Res. 28(11), 2234-2241.

Chadd, H.E. and Chamow, S.M. (2001) Therapeutic antibody expression technology. Curr. Opin. Biotechnol. 12(2), 188-194.

Chambers, T.J., Owens, J.M., Hattersley, G., Jat, P.S. and Noble, M.D. (1993) Generation of osteoclast-inductive and osteoclastogenic cell lines from the H2KbtsA58 transgenic mouse; Proc. Natl. Acad. Sci. USA 90(12), 5578-5582.

Cianfriglia, M., Marian, M., Armellini, D., Massone, A., Lafata, M., Presentini, R. and Antonio, G. (1986) Methods for high frequency production of soluble antigen-specific hybridomas; specificities and affinities of the monoclonal antibodies obtained. Methods in Enzymol. 121, 193-210.

Cianfriglia, M., Nuti, M., Turchi, V., Barca, S., Tombesi, M., Morrone, S., Cenciarelli, C. and Natali, P.G. (1987) High frequency production of hybridomas secreting antibodies to cell antigens. Hybridoma 6(6), 673-677. Abstract.

Citri, Y., Braun, J. and Baltimore, D. (1987) Elevated myc expression and c-myc amplification in spontaneously occurring B lymphoid cell lines. J. Exp. Med. 165(4), 1188-1194.

Clackson, T., Yang, W., Rozamus, L.W., Hatada, M., Amara, J.F., Rollins, C.T., Stevenson, L.F., Magari, S.R., Wood, S.A., Courage, N.L., Lu, X., Cerasoli k, F., Gilman, M. and Holt, D. (1998) Redesigning an FKBP-ligand interface to generate chemical dimerizers with novel specificity. Proc. Natl. Acad. Sci. USA 95, 10434-10442.

Clark, M.R. and Milstein, C. (1981) Expression of spleen cell immunoglobulin phenotype in hybrids with myeloma cell lines. Somatic Cell Genet. 7(6), 657-666.

Coller, H.A. and Coller, B.S. (1986) Poisson statistical analysis of repetitive subcloning by the limiting dilution technique as a way of assessing hybridoma monclonality. Methods in Enzymol. 121, 412-417.

Collins, J.J., Black, P.H., Strosberg, A.D., Haber, E. and Bloch, K.J. (1974) Transformation by Simian Virus 40 of spleen cells from a hyperimmune rabbit: Evidence for synthesis of immunoglobulin by the transformed cells. Proc. Natl. Acad. Sci. USA 71(12), 260-262.

Conrad, M. K. and Lo, M.M.S. (1990) Facilitated cell fusion for hybridoma production. Methods in Enzymol. 184. 641-653, Davis, J.M. (1980) A single-step technique for selecting and cloning hybridomas for monoclonal antibody production. Methods in Enzymol. 121, 307-322.

De Blas, A.L., Ratnaparkhi, M.V. and Mosimann, J E (1983) Estimation of the number of monoclonal hyhridomas in a cell-fusion experiment, Methods in Enzymol. 92, 36-39.

Dangl, J.L. and Herzenberg, L.A. (1982) Selection of hybridomas and hybridoma variants using the fluorescence activated cell sorter. J Immunol. Methods 52(1), 1-14.

Dennis, J.E. and Caplan, A.L. (1996) Analysis of the developmental potential of conditionally immortal marrow-derived mesenchymal progenitor cells isolated from the H-2Kb-tsA58 transgenic mouse, Conned Tissue Res. 35(1-4), 93-99. Abstract.

Duffey, P.S., Drouillard, D.L. and Barbe, C.P. (1981) Lymphocyte sorting on albuminated CIBA blue dextran-staphylococcal protein A-conjugated sepharose 6MB affinity columns. J. Immunol. Methods 45(2), 137-151.

Erickson, L.D., Tygrett, L.T., Bhatia, S.K., Grabstein, K.H. and Walderscmidt, T.J. (1996) Differential expression of CD22 (Lyb8) on murine B cells. Differential expression of CD22 (Lyb8) on murine B cells. Int. Immunol. 8(7), 1121-1129.

Faller, G., Vollmers, H.P., Weiglein, L. Marx. A., Zink, C., Pfaff, M. and Muller-Hermelink, H.K. (1990) HAB-1, a new heteromyeloma for continuous production of human monoclonal antibodies. Br. J Cancer 62(4), 595-598.

Ferreira, A. and Kosik, K.S. (1996) Accelerated neuronal differentiation induced by p53 suppression. J. Cell Sci. 109, 1509-1516.

Ferraro, A.S. and Newkirk, M.M. (1993) In vitro stimulation of human peripheral blood B cells from normal individuals by activated T cells increases the efficiency of hybridoma generation. Hum. Antibodies Hybridomas 4(2), 8085. Abstract.

Fielden, M.R. and Zacharewski, T.R. (2001) Challenges and limitations of gene expression profiling in mechanistic and predictive toxicology. Toxicol. Sci. 60(1), 6-10.

Foung, S.K. and Perkins, S. (1989) Electric field-induced cell fusion and human monoclonal antibodies. J. Immunol. Methods 116(1), 117-122.

Foung, S., Perkins, S., Kafadar, K., Gessner, P. and Zimmerman, U. (1990) Development of microfusion techniques to generate human hybridomas. J Immunol. Methods 134(1), 35-42.

Fuchs, S.Y., Adler, V., Wu, X. Ronai, Z. (1998) Mdm2 association with p53 targets itsubiquitination. Oncogene 17(19), 2543-2547.

Gauwerky, C.E., Haluska, F.G., Tsujimoto, Y., Nowell, P.C. and Croce, C.M. (1988) Evolution of B-cell malignancy: Pre-B-cell leukemia resulting from MYC activation in a B-cell neoplasm with a rearranged BCL2 gene. Proc. Natl. Acad. Sci. USA 85(22), 8548-8552.

Gray, F., Kenney, J.S. and Dunne J.F. (1995) Secretion capture and report web: use of affinity derivâtized agarose microdroplets for the selection of hybridoma cells. J Immunol. Methods 182, 155-163.

Green, L.L., Hardy, M.C., Maynard-Currie, C.E., Tsuda, H., Louie, D.M., Mendez, M.J., Abderrahim, H., Noguchi, M., Smith, D.H. and Zeng, Y et al. (1994) Antigen-specific human monoclonal antibodies from mice engineered with human Ig heavy and light chain YACs. Nat. Genet. 7(1),13-21.

Greenstein, J.L. Leary, J., Horan, P., Kappler, J.W. and Marrack, P. (1980) Flow sorting of antigen-binding B cell subsets. J. Immunol. 124(3), 1472-1481.

Hardy, R.R., Carmack, C.E., Shinton, S.A., Kemp, J.D. and Hayakawa, K. (1991) Resolution and characterization of Pro-B and Pre-Pro-B cell stages in normal mouse bone marrow. J. Exp. Med. 173(5), 1213-1225.

Hariharan, I.K., Harris, A.W., Crawford, M., Abud, H., Webb, E., Cory, S. and Adams, J.M. (1989) A bcr-v-abl oncogene induces lymphomas in transgenic mice. Mol. Cell Biol. 9(7), 2798-2805.

Harris, A.W., Bath, M.L., Rosenbaum, H., McNeall, J., Adams, J.M. and Cory, S. (1990) Lymphoid tumorigenesis by v-abl and BCR-v-abl in transgenic mice. Curr. Top. Microbiol. Immunol. 166, 165-173.

Haupt, Y., Maya, R., Kazaz, A. and Oren, M. (1997) Mdm2 promotes the rapid degradation of p53. Nature 387, 296-299.

Hennigan, R.F. and Stambrook, P.J. (2001) Dominant negative c-jun inhibits activation of the cyclin D1 and cyclin E kinase complexes. Mol. Biol. Cell. 12, 2352-2363.

Hewish, D.R. and Werkmeister, J.A. (1989) The use of an electroporation apparatus for the production of murine hybridomas. J. Immunol. Methods 120(2), 285-289.

Hollyoake, M., Stuhler, A., Farrell, P., Gordon, J. and Sinclair, A. (1995) The normal cell cycle activation program is exploited during the infection of quiescent B lymphocytes by Epstein-Barr virus. Cancer Res. 55(21), 4784-4787.

Hoven, M. Y., De Leij, L., Keij, J.F. and The, T.H. (1989) Detection and isolation of antigen-specific B cells by the fluorescence activated cell sorter (FACS). J. Immunol. Methods 117(2), 275-284.

Hui, S,W. and Stenger, D.A. (1993) Electrofusion of cells: Hybridoma production by electrofusion and polyethylene glycol. Methods in Enzymol. 220, 212-227.

Igarashi, M. and Bando, Y. (1990) Enhanced efficiency of cell hybridization by neuramidase treatment. J. Immunol. Methods 135(1-2), 91-93.

Jacks, T., Remington L., Williams, B.O., Schmitt, E.M., Halachmi, S., Bronson, R.T. and Weinberg, R.A. (1994) Tumor spectrum analysis in p53-mutant mice. Curr. Biol. 4(1), 1-7.

Jantschelf, P., Winkler. L., Karawajew, L., Kaiser, G., Bottger, V. and Micheel, B. (1993) Hybrid hybridomas producing bispecific antibodies to CEA and peroxidase isolated by a combination of HAT medium selection and fluorescence activated cell sorting. J. Immunol: Methods 163(1), 91-97.

Jagger, D.J., Griesinger, C.B., Rivolta, M.N., Holley, M.C. and Ashmore, J.F. (2000) Calcium signalling mediated by the alpha-9 acetylcholine receptor in a cochlear cell line from the Immortomouse. J. Physiol. 527.1, 49-54.

Jahn, S., Grunow, J.S., Kiessig, S.T., Settmacher, U. and Von Baehr, R. (1990) Strategies in the development of human monoclonal antibodies. Dey. Biol. Stand. 71, 3-7, Abstract.

Jahn, S., Walper, J.S., Grunow, R., Heym, S., Volk, H.D. and von Baehr, R. (1990) The hybridization of EBV-immortalized human B-lymphocytes with a human-mouse heteromyeloma cell line. Allerg. Immunol. (Leipz) 36(4), 359-365. Abstract.

Jat, P.S., Noble, M.D., Ataliotis, Y., Tanaka, N., Yannoutsos, L., Larsen L. and Kioussis, D. (1991) Direct derivation of conditionally immortal cell lines from an H2Kb-tsA58 transgenic mouse. Proc. Natl. Acad. Sci. USA 88, 5096-5100.

Jat, P.S. and Sharp, P.A. (1989) Cell lines established by a temperature-sensitive Simian virus 40 large-T-antigen gene are growth restricted at the nonpermissive temperature. Mol. (Cell Biol. 9(4). 1672-1681.

Kanda. S., Lerner, E.C., Tsuda, S., Shono, T., Kanetake, H. and Smithgall, T.E. (2000) The nonreceptor protein-tyrosine kinase c-Fes is involved in fibroblast growth factor-2-induced chemotaxis of murine brain capillary endothelial cells. J. Biol. Chem. 275(14), 10105-10111.

Kanki, T. and Takeuchi, S. (1995) Immortalization of plasma cells by plasmid DNA and its hybridoma. Hum. Antibodies Hybridomas 6(3). 89-92. Abstract.

Karawajew, L. Miceel, B., Behrsing, O. and Gaestel, M. (1987) Bispecific antibody-producing hybrid hybridomas selected by a fluorescence activated cell sorter. J. Immunol. Methods 96(2), 265-270.

Karawajew, L. Rudchenko, S., Wlasik, T., Trakht, I. and Rakitskaya, V. (1990) Flow sorting of hybrid hybridomas using the DNA stain Hoechst 33342. J. Immunol. Methods 129(2) 277-282.

Karns, L.R., Kisielewski, A., Guiding, K.M., Seraj, J.M. and Theodorescu, D. (2001) Measurement of gene expression by an ecdysone-inducible gene switch in tumor xenografts. BMC Biotechnology 1, 11-22.

Karsten, U., Stoney. P. and Seidel, B. 1993) Polyethylene glycol and electric field-mediated cell fusion for formation of hybridomas. Methods in Enzymol. 220, 228-238.

Kawahara, H., Yamada, K., Shirahata, S. and Murakami, H. (1990) A new human fusion partner, HK-128, for making human-human hybridomas producing monoclonal IgG antibodies. Cytotechnology 4(2), 139-143. Abstract.

Kenney, J.S., Gray, F., Ancel, M.H. and Dunne, J.F. (1995) Production of monoclonal antibodies using a secretion capture report web. Biotechnology (N.Y.) 13(8), 787-790. Abstract.

Kohler, G. and Milstein, C. (1975) Continuous cultures of fused cells secreting antibody of predefined specificity. Nature 256, 495-497.

Kovalchuk, A.L., Qi, C.F., Torrey, T.A., Taddesse-Heath, L., Feigenbaum, L., Park, S.S., Gerbitz, A., Klobeck, G., Hoertnagel, K., Polack, A., Bornkamm, G:W., Janz, S. and Morse, H.C. 3rd (2000) Burkitt lymphoma in the mouse. J. Exp. Med. 192(8), 1183-1190.

Kreitman, R.J., Wilson, W.H,, Bergeron, K., Raggio, M., Stetler-Steyenson, M., FitzGerald, D.J. and Patsan, I. (2001) Efficacy of the anti-CD22 recombinant immunotoxin BL22 in chemotherapy-resistant hairy-cell leukemia, N. Engl. J Med. 345, 241-247.

Kumar, A., Ta, D., Henderson, D., Mushinski, J.F., Reed, J.C., Kuus-Reichel, K. and Saedi, M.S. (1999) bc 12 and v-abl oncogenes cooperate to immortalize murine B cells that secrete antigen specific antibodies. Immunol. Lett. 65(3), 153459.

Lane, R.D. (1985) A short-duration polyethylene glycol fusion technique for increasing production of monoclonal antibody-secreting hybridomas.J. Immunol. Methods 81(2), 223-228.

Lane, R.D., Crissman, R.S. and Ginn, S. (1986) High efficiency fusion procedure for producing monoclonal antibodies against weak immunogens. Methods in Enzymol. 121, 183-192.

Lane, R.D., Crissman, R.S. and Lachman, M.F. (1984) Comparison of polyethylene glycols as fusogens for producing lymphocyte-myeloma hybrids. J. Immunol. Methods 72(1), 71-76.

Langdon, W.Y., Haris, A.W., Cory, S. and Adams, J.M. (1986) The c-myc oncogene perturbs B lymphocyte development in E-mu-myc transgenic mice. Cell 47(1), 11-18.

Liu, B. Y., Guo, J., Lanske, B., Divieti, P., Kronenberg, H.M. and Bringhurst, F.R. (1998) Conditionally immortalized murine bone marrow stromal cells mediate parathyroid hormone-dependent osteoclastogenesis in vitro. Endocrinology 139(4), 1952-1964.

Lo, M.M, Tsong, T.Y., Conrad, M.K., Strittmatter, S.M., Hester, L.D. and Snyder. S.H. (1984) Monoclonal antibody production by receptor-mediated electrically induced cell fusion, Nature 310(5980), 792-794.

Lundkvist, A., Horling, J., Athlin, L., Rosen, A. and Niklasson, B. (1993) Neutralizing human monoclonal antibodies against Puumala virus, causative agent of nephropathia epidemica: A novel method using antigen-coated magnetic beads for specific B cell isolation. J. Gen. Virol. 74(7), 1303-1310.

Malynn, B.A., de Alboran, I.M., O'Hagan, R.C., Bronson, R., Davidson. L., DePinho, R.A. and Alt, F.W. (2000) N-myc can functionally replace c-myc in marine development, cellular growth and differentiation. Genes Dev. 14(11), 1390-1399.

Manickan, E., Satoi, J., Wang, T.C. and Liang, T.J. (2001) Conditional liver-specific expression of simian virus 40 T antigen leads to regulatable development of hepatic neoplasm in transgenic mice. J. Biol. Chem. 276(17), 13989-13994.

Marder, P., Maciak, R.S,, Fouts, R.L., Baker, R.S. and Starling, J.J. (1990) Selective cloning of hybridotna cells for enhanced immunoglobulin production using flow cytometric cell sorting and automated laser nephelometry. Cytometry 11(4), 498-505.

Marusich, M.F. (1988) Efficient hybridoma production using previously frozen splenocytes. J. Immunol. Methods 114(1-2), 155-159.

Matsushita, H., Morishita, R., Aoki, M., Tomita, N., Taniyama, Y., Nakagami, H., Shimozato, T., Higaki, J., Kaneda, Y and Ogihara, T. (2000) Transfection of antisense p53 tumor suppressor gene oligodeoxynucleotides into rat carotid artery in abnormal growth of vascular smooth muscle cells. Circulation 101, 1447-1452.

Metcalf. D., Nossal, G.J., Warner, N.L., Miller, J.F., mandel, T.E., Layton, J.E. and Gutman, G.A. (1975) Growth of B-lymphocyte colonies in vitro. J Exp. Med. 142(6), 1534-1549.

Mendez, M.J., Green, L.L., Corvalan, J.R., Jia, X.C., Maynard-Currie, C.E., Yang, X.D., Gallo, M.L., Louie, D.M., Lee, D.V., Erickson, K.L., Luna, J., Roy, C.M., AbderraHm, H., Kirschenbaum, F., Noguchi, M., Smith, D.H., Fukushima, A.,. Hales, J.F., Klapholz, S., Finer, M.H., Davis, C.G., Zsebo, K.M. and Jakobovits, A. (1997) Functional transplant of megabase human immunoglobulin loci recapitulates human antibody response in mice. Nature Genetics, 15(2),146-156.

Moore, L.R., Zborowski, M., Sun., L. and Chalmers, J.J. (1998) Lymphocyte fractionation using immunomagnetic colloid and a dipole magnet flow cell sorter. J. Biochem. Biophys. Methods 37(1-2), 11-33.

Mostecki, J., Halgren, A., Radfar, A., Sachs, Z., Ravitz, J., Thome, K.C. and Rosenberg, N. (2000). Loss of heterozygosity at the Ink-4a/Arf locus facilitates abelson virus transformation of pre-B cells. J. Virol. 74(20), 9479-9487.

Niedbla, W.G. and Stott, D.I. (1998) A comparison of three methods for production of human secreting autoantibodies. Hybridoma 17(3), 299-304. Abstract.

Noble, M., Groves, A.K., Ataliotis, P., Ikram, Z. and Jat, P.S.(1995) The H-2K$^b$tsA58 transgenic mouse: A new tool for the rapid generation of novel cell lines. Transgenic Res. 4(4), 215-225.

O'Hare, M.J., Bond, J., Clarke, C., Takeuchi, Y., Atherton, A.J., Berry, C., Moody, J., Silver, A.R.J., Davies, D.C., Alsop, A.E., Munro Neville, A. and Jat, P.S., (2001) Conditional immortalization of freshly isolated human mammary fibroblasts and endothelial cells. Proc. Natl. Acad. Sci. USA 98(2), 646-651.

Ojwang, J.O., Hampel, A., Looney, D.J., Wong-Staal, F. and Rappaport, J. (1992) Inhibition of human immunodeficiency virus type I expression by a hairpin ribozyme. Proc. Natl. Acad. Sci. USA 89, 10802-10806.

Overell, R.W., Weisser, K.E., Hess, B., Namen, A.E. and Grabstein, K.H. (1989) Stage-specific transformation of murine B lineage cells by ras and myc. Oncogene 4(12), 1425-1432.

Palomo, C., Zou, X., Nicholson, I.C., Butzler, C. and Bruggemann, M. (1999) B-Cell tumorigenesis in mice carrying a yeast artificial chromosome-based Immunoglobulin Heavy/c-myc translocus is independent of the heavy chain enhancer (Eµ). Cancer Research 59, 5625-5628.

Panova, L and Gustafsson, B. (1995) Increased human hybridoma formation by electrofusion of human B cells with heteromyeloma SPAM-8 cells. Hybridoma 14(3), 265-269. Abstract.

Parks, D.R., Bryan, V.M., Oi, V.T. and Herzenberg, L.A. (1979) Antigen-specific identification and cloning of hybridomas with a fluorescence-activated cell sorter. Proc. Natl. Acad. Sci (USA) 76(4), 1962-1966.

Pasqualucci, L., Neumeister, P., Goossens, T., Nanjangud, G., Chaganti, R.S., Kuppers, R. and Dalla-Favera, R. (2001) Hypermutation of multiple proto-oncogenes in B-cell diffuse large-cell lymphomas. Nature 412(6844), 341-346.

Pelicci, P.G., Knowles, D.M. 2nd, Arlin, Z.A., Wieczorek, R., Luciw, P., Dina, D., Basilico, C. and Dalla-Favera, R. (1986) Multiple monoclonal B cell expansions and c-myc oncogene rearrangements in acquired immune deficiency syndrome-related lymphoproliferative disorders. Implications for lymphomagenesis. J. Exp. Med. 164(6), 2049-2060.

Radna, R.L., Caton, Y., Jha, K.K., Kaplan, P., Li, G., Traganos, F. and Ozer, H.L. (1989) Growth of immortal simian virus 40 tsA-transformed human fibroblasts is temperature dependent. Mol. Cell Biol. 9(7), 3093-3096.

Raymon, H.K., Thode, S., Zhou, J., Friedman, G.C., Pardinas, J.R., Barrere, C., Johnson, R.M. and Sah, D.W.Y. (1999) Immortalized human dorsal root ganglion cells differentiate into neurons with nociceptive properties J. Neurosci. 19(13), 5420-5428.

Reason, D., Carminati, J., Kimura, J. and Henry, C. (1987) Directed fusion in hybridoma production. J. Immunol. Methods 99(2), 253-257.

Rivera, V.M., Clackson, T., Natesan, S., Pollock, R., Amara, J.F., Keenan, T., Magari, S.R., Philips, T., Courage, N.L., Cerasoli Jr, F., Holt, D.A. and Gilma, M. (1996) A humanized system for pharmacologic control of gene expression. Nature (medicine) 2(9), 1028-1032.

Rosenbaum, H., Harris, A.W., Bath, M.L., McNeall, J., Webb, E., Adams, J.M. and Cory, S. (1990) An Eµ-v-abl transgene elicits plasmacytomas in concert with an activated myc gene. EMBO J 9(3), 897-905.

Rosenbaum, H., Webb, Adams, J.M., Cory, S., and Harris, A.W. (1989) N-myc transgene promotes B lymphoid proliferation, elicits lymphomas and reveals cross-regulation with c-myc. EMBO J 8(3), 749-755.

Ryding A.D.S., Sharp, M.G.F. and Mullins, J.J. (2001) Conditional transgenic technologies. J. Endocrin. 171, 1-14.

Sadigh, S., Scott, B.B., Mageed, R.A., Malcolm, A., Andrew, E.M. and Main, RN. (1994) Identification of hybridomas derived from mouse CD5+ B lymphocytes by fluorescent staining for cytoplasmic CD5 expression. Immunology 81(4), 558-563.

Saez, E., Nelson, M.C., Eshelman, B., Banayo, E., Koder, A., Cho, G.J. and Evans, R.M. (2000) Identification of ligands and coligands for the ecdysone-regulated gene switch. Proc. Natl. Acad. Sci. USA 97(26), 14512-14517.

Sethupathi, P., Spiecker-Polet,H., Polet, H.,Yam. P.C., Tunyaplin, C. and Knight, K.L. 0994) Lymphoid and non-lymphoid tumors in EK myc transgenics. Leukemia 8(12), 2144-2155.

Siraganian, R.P., Fox, P.C. and Berenstein, E.H. (1983) Methods of enhancing the frequency of antigen-specific hybridomas. Methods in Enzymol. 92,17-26.

Spieker-Polet, H., Sethupathi, P., Yam, P-C. and Knight, K.L. (1995) Rabbit monoclonal antibodies: Generating a fusion partner to produce rabbit-rabbit hybridomas, Proc. Natl. Acad. Sci. USA 92, 9348-9352.

Srinivas, P.S., Srivastava, S., Hanash, S. and Wright, G.L. Jr. (2001) Proteomics in early detection of cancer. Clin. Chem. 47(10), 1901-1911.

Stahl, C., Staehelin, T. and Miggiano, V. (1983) Spleen cell analysis and optimal immunization for high-frequency production of specific hybridomas. Methods in Enzymol. 92, 26-36.

Stanton, L.W., Watt, R. and Marcu, K.B. (1983) Translocation, breakage and truncated transcripts of c-myc oncogene in murine plasmacytomas. Nature 303. 401-406.

Steenbakkers, P.G.A., van Meet, F.C.M. and Olijve, W. (1992) A new approach to the generation of human or murine antibody producing hybridomas. J. Immunol. Methods 152, 69-77.

Steenbakkers, P.G.A., van Wezenbeek. P.M. and Olijve, W. (1993) Immortalization of antigen selected B cells. J. Immunol. Methods 163(1), 33-40.

Strosberg, A.D., Collins, J.J., Black, P.H., Malamud, D., Wilbert, S., Bloch, K.J. and Haber, E. (1974) Transformation by simian virus 40 of spleen cells from a hyperimmune rabbit: Demonstration of production of specific antibody to the immunizing antigen. Proc Natl. Acad. Sci. USA 71(2), 263-264.

Sugiyama, H., Wang, Y., Jackson, P., Sawyers, C.L. and Klein, G (1994) Molecular requirements for rapid plasmacytoma and pre-B lymphoma .induction by Abelson murine leukamia virus in myc-transgenic mice. Int. J. Cancer 58(1). 135-141.

Symonds, H.S., McCarthy, S.A., Chen, J., pipas, J.M. and Van.Dyke, T. (1993) Use of transgenie mice reveals cell-specific transformation by a simian virus 40 T-antigen amino-terminal mutant. Mol. Cell. Biol. 13(6), 3255-3265.

Taggart, R.T. and Samloff, I.M. (1982) Stable antibody-producing hybridomas. Science 219, 1228-1230.

Tavelin, S., Milovic, V., Ocklind, G., Olsson, S. and Artursson, P. (1999) A conditionally immortalized epithelial cell line for studies of intestinal drug transport. J. Pharmacol. Exp.Therapeut. 290(3), 1212-1221.

Tomita, M. and Tsong, T.Y. (1990) Selective production of hybridoma cells: Antigenic-based pre-selection of B lymphocytes for electrofusion with myeloma cells. Biochim. Biophys. Acta 1055(3), 199-206, Abstract Only.

Tsong, T.Y. and Tomita, M. (1993) Selective B lymphocyte-myeloma cell fusion. Methods in Enzymol. 220, 238-246.

Tsuchiyama, L., Kieran, J., Boyle, P. and Wetzel, G.D. (1997) Synergy between anti-CD40 MAb and Epstein-Barr virus in activation and transformation of human B lymphocytes. Hum. Antibodies 8(1), 43-47. Abstract.

van Duijn, G., Langedijk, J.P., de Boer, M. and Tager, J.M. (1989) High yields of specific hybridomas obtained by electrofusion of murine lymphocytes immunized in vivo or in vitro. Exp. Cell Res. 183(2), 463-472. Abstract.

Van Mourik, P., Rivero, R.A., van der Kwast, T.H., Lansdorp, P.M. and Zeijlemaker, W.P. (1984) Density separation of spleen cells increases fusion frequency and yield of Ig-producing hybridomas, J.Immunol. Methods 68, 45-53.

Virley, D., Ridley, R.M., Sinden, J.D., Kershaw, T.R., Harland, S., Rashid, T., French, S., Sowinski, P., Gray, J.A., Lantos, P.L. and Hodges, H. (1999) Primary CAI and conditionally immortal MHP36 cell grafts restore conditional discrimination learning and recall in marmosets after excitotoxic lesions of the hippocampal CA1 field. Brain 122, 2321-2335.

Wang, Y., DeMayo, F.J., Tsai, S.Y., O'Malley, B.W. (1997a) Ligan-inducible and liver-specific target gene expression in transgenic mice. Nature Biotechnol, 15(3), 23 9-243.

Werkmeister, J.A. et al., (1991) The use of peptide-mediated electrofusion to select monoclonal antibodies directed against specific and homologous regions of the potyvirus coat protein J. Immunol. Methods 143(2), 151-157.

Westerwoudt, R.J. (1985) Improved fusion methods. IV. Technical aspects. J. Immunol. Methods 77(2), 181-196.

Westerwoudt, R.J. (1986) Factors affecting production of monoclonal antibodies. Methods in Enzymol. 121, 3-18.

Whitehead, R.H., VanEeden, P.E., Noble, M.D., Ataliotis, P. and Jat, P.S. (1993) Establishment of conditionally immortalized epithelial cell lines from both colon and small intestine of adult $H-2K^b$-tsA58 transgenic mice. Proc. Natl. Acad. Sci. USA 90, 587-591.

Xirodimas, D., Saville, M.K., Edling, C., Lane, D.P. and Lain, S. (2001) Different effects of p14ARF on the levels of ubiquitinated p53 and Mdm2 in vivo. Oncogene 20, 4972-4983.

Zhang, G., Slaughter, C. and Humphries, E.H. (1995) v-rel induces ectopic expression of an adhesion molecule, DM-GRASP, during B-lymphoma development. Mol. Cell Biol. 15(3), 1806-1816.

* cited by examiner

SEQUENCE LISTING

<160> NUMBER OF SEQ ID NOS: 16

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: DNA primer
<220> FEATURE:
<221> NAME/KEY: primer_bind
<222> LOCATION: (1)..(29)
<223> OTHER INFORMATION: 5' VgEcR-RXR DNA primer containing SpeI
      restriction enzyme recognition site.

<400> SEQUENCE: 1
gtactagtag ggattttggt catggctag                                29

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: Complement((1)..(30))
<223> OTHER INFORMATION: 3' VgEcR-RXR DNA primer containing SpeI
      restriction enzyme recognition  site.

<400> SEQUENCE: 2
gtactagtca gctggttctt tccgcctcag                                30

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: (1)..(36)
<223> OTHER INFORMATION: 5' c-myc DNA primer containing NheI restriction
      enzyme recognition site.

<400> SEQUENCE: 3
gtagctagcg ccaccatgcc cctcaacgtg aacttc                         36

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: Complement((1)..(30))
<223> OTHER INFORMATION: 3' c-myc DNA primer containing XhoI restriction
      enzyme recognition site.

<400> SEQUENCE: 4
gatctcgagt tatgcaccag agtttcgaag                                30

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence:DNA primer
<220> FEATURE:

```
<221> NAME/KEY: primer_bind
<222> LOCATION: (1)..(36)
<223> OTHER INFORMATION: 5' ab1 DNA primer containing NheI restriction
      enzyme recognition site.

<400> SEQUENCE: 5
gtagctagcg ccaccatgga gcctggtgga gttggc                                   36

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: Complement((1)..(30))
<223> OTHER INFORMATION: 3' ab1 DNA primer containing XhoI restriction
      enzyme recognition  site.

<400> SEQUENCE: 6
gatctcgagt caagcttgct gtccaagatc                                          30

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: (1)..(37)
<223> OTHER INFORMATION: 5' SV40 Large T DNA primer containing NheI
      restriction enzyme recognition site.

<400> SEQUENCE: 7
gtagctagcg ccaccatgga tagagttctg agcagag                                  37

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: Complement((1)..(30))
<223> OTHER INFORMATION: 3' SV40 Large T DNA primer containing XhoI
      restriction enzyme recognition site.

<400> SEQUENCE: 8
gatctcgagt caataaactg tgtattcagc                                          30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: (1)..(30)
<223> OTHER INFORMATION: 5' pIND DNA primer containing SpeI restriction
      enzyme recognition site.

<400> SEQUENCE: 9
gtactagttg ccacctgacg tcgacggatc                                          30

<210> SEQ ID NO 10
<211> LENGTH: 29
```

-continued

```
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: Complement((1)..(29))
<223> OTHER INFORMATION: 3' pIND DNA primer containing SpeI restriction
      enzyme recognition site.

<400> SEQUENCE: 10
gtactagtct cagaagccat agagcccac                                              29

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: (1)..(32)
<223> OTHER INFORMATION: 5' beta-globin DNA primer.

<400> SEQUENCE: 11
ccaatctgct cacacaggat agagagggca gg                                          32

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: Complement((1)..(32))
<223> OTHER INFORMATION: 3' beta-globin DNA primer.

<400> SEQUENCE: 12
ccttgaggct gtccaagtga ttcaggccat cg                                          32

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: (1)..(21)
<223> OTHER INFORMATION: 5' c-myc transgene confirmation DNA primer.

<400> SEQUENCE: 13
acagcttcga aactctggtg c                                                      21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: (1)..(21)
<223> OTHER INFORMATION: 5' abl transgene confirmation DNA primer.

<400> SEQUENCE: 14
agctgccctg cacctttcct g                                                      21

<210> SEQ ID NO 15
```

```
<211> LENGTH: 21
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: (1)..(21)
<223> OTHER INFORMATION: 5' Large T transgene confirmation DNA primer.

<400> SEQUENCE: 15
aacttggctc ctccgatgct c                                          21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:DNA primer
<220> FEATURE:
<221> NAME/KEY: primer_bind
<222> LOCATION: (1)..(21)
<223> OTHER INFORMATION: 5' VgEcR-RXR transgene confirmation DNA primer.

<400> SEQUENCE: 16
cagctgcatt ctcccatcag c                                          21
```

METHOD FOR PRODUCING IMMORTALISED ANTIBODIES-SECRETING CELLS

The invention describes methods for the isolation of clonal cell lines secreting an antibody of choice from a transgenic mouse. In one embodiment of the invention the transgenic animal is an 'Immortomouse'. In a second embodiment it is one in which inducible expression of an oncogene(s) or a combination of oncogene(s) with a gene expressing antisense directed to a tumour suppressor sequence or a gene whose product inactivates a tumour suppressor protein, or a transgenic mouse in which the tumour suppressor gene has been inactivated, are expressed in a suitable combination. In all cases the purpose being to derive monoclonal antibodies without the requirement for fusing antibody-secreting cells, such as spleen cells, with myelomas to produce hybridomas. In a further embodiment of the invention the production of humanised antibodies is achieved by breeding the transgenic mice described herein with those in which the mouse Ig locus has been humanised.

The invention describes a method for the production of monoclonal antibodies (mAbs) from transgenic mice. This method provides a significant improvement over the widely used mAb methodology originally described by Kohler and Milstein in 1975, the core technology of which has remained largely unmodified since. In essence the methods of the invention described herein will provide a more rapid and efficient means of producing monoclonal antibodies and humanised monoclonal antibodies for research and therapeutic use, by the elimination of the myeloma/spleen-cell fusion step.

BACKGROUND OF THE INVENTION

Monoclonal antibodies are utilised widely in both the academic and commercial pharmaceutical and biotechnology sectors. They are used to detect specific entities, commonly referred to as antigens, such as—but not exclusively—proteins or peptides, through an interaction with a specific site on that entity known as the epitope. The same epitope may be found on different proteins, similarly any one protein may display several different epitopes. Such reagents are commonly used in basic research, diagnostic, assay development and more recently therapeutic applications.

Antibody specificity is defined as the degree to which an antibody will recognise and distinguish one epitope (or subset of epitopes) from a diverse repertoire of other epitopes. Although the absolute degree of specificity required of the antibody may be application specific, it is generally the case that the investigator desires maximum specificity from the antibody, thus minimising the likelihood of obtaining false results as a consequence of non-specific interactions. The greater the requirement for specificity, the more challenging it can become to generate such a reagent. Thus it follows that improvements in the efficiency of producing, selecting and cloning cells which secrete monoclonal antibodies will increase the likelihood of being able to obtain a reagent with the required application-specific characteristics.

Although well established and widely utilised, the fundamental method for producing antibodies by fusing splenic lymphocytes with myeloma cells has remained largely unmodified for the past 25 years. Due to some of the limitations inherent in this technique, many new technologies have been developed to produce protein (antigen/epitope) recognition reagents with similar characteristics—and in some cases structures—to the traditional monoclonal antibody. These include phage display, phagemid display, scFV and others (Adams and Schier 1999; Walter et al. 2001). Despite the potential advantages and promise of many of these new technologies, antibodies produced by the hybridoma method—or a modification thereof—developed by Kohler and Milstein (1975) remains the method of choice in most in-house and contract laboratories. Thus an advance which significantly improves the efficiency, reliability and ultimately the likelihood of engineering a useful reagent via this method—as described in this invention—provides a significant breakthrough.

Current Methods of Producing Monoclonal Antibodies and their Limitations

Activation of β-lymphocytes can lead to the production of an antibody specific for a given antigen. However the utility of these β-lymphocytes is limited for in vitro antibody reagent production as such cells are short-lived in cell culture (Kohler and Milstein 1975). Thus methods have been developed to enable these antibody secreting cells to survive in culture by fusing them with immortalised cell lines (myelomas), which themselves can grow indefinitely in culture. Many of the myeloma lines used today were originally antibody-secreting themselves, such as Sp2 cells. Thus the challenge faced by the pioneers of monoclonal antibody technology was threefold: 1) to develop appropriate immortalised cell lines which themselves secrete no antibodies but would enable immortalised growth of a myeloma/β-lymphocyte hybridoma, 2) to optimise the fusion of the β-lymphocyte and myeloma line, and 3) to devise a method of selecting hybridoma cells over both non-fused myeloma and β-lymphocyte cells. Kohler and Milstein in (1975) were the first to describe a method which achieved these goals by fusing the β-lymphocyte with a myeloma line using Sendai virus. Later it was discovered that polyethylene glycol (PEG) could achieve the same aim. PEG is widely used today as the fusion agent of choice; the reagent often referred to as the 'fusogen'.

The host used for monoclonal antibody production is in most cases a Balb/c or Balb/c hybrid mouse, since most of the myeloma cell lines are derived from Balb/c mice. The antigen may be a peptide, pure protein, partially purified protein or perhaps a non-purified tissue sample. It may also be soluble or insoluble. The immunisation schedule often involves the co-injection of an adjuvant such as freunds to assist in the induction of an immune response. Additionally less immunogenic antigens and peptides are often coupled to a carrier such as key-hole lympet haemocyanin (KLH) to increase their immunogenicity. The immunogenicity defining the likelihood that the antigen will induce the required immune response. The progress of the immune response is measured by taking serum samples throughout the schedule and testing—by methods such as enzyme linked immunoabsorbent assays (ELISA) or western blotting—for the presence of antibodies specific for the antigen of interest. Once a strong immune response against the antigen of interest has been detected the, β-lymphocytes (usually from spleen) are harvested and fused with the myelomas. The precise timing of the spleen harvest with respect to the final immunisation, can influence the efficiency of the fusion (Stahl et aL 1983; Cianfriglia et al. 1986; Cianfriglia et al. 1987).

The Fusion

The success of the fusion between the spleen derived β-lymphocytes and the myeloma cell line may be controlled—at least to some extent—by a number of factors. These include, although not exclusively; the fusogen, temperature, cell mixing protocol, ratio of spleen to myeloma cells, time of fusion, cell fusion recovery protocol, media/buffer batches and of course the investigator. The precise details of the protocol and success of the fusion often vary from laboratory to laboratory and even from experiment to experiment (Igarashi and Bando, 1990).

The fusion is catalysed by the addition of polyethylene glycol (PEG) to a suspension of spleen and myeloma cells. The success of the procedure is very much dependent on the skill and experience of the operator, as the freshly fused cells are sensitive to mechanical and chemical disruption. The method of PEG addition to the cells and the formulation of PEG used has been optimised to achieve fusion frequency of around $6 \times 10^{-6}$ to $3 \times 10^{-5}$ (Lane et al. 1984; Lane 1985; Lane et al. 1986). The fusion frequency being defined as the number of hybridomas generated divided by the number of lymphocyte cells used in the fusion (approximately $1 \times 10^8$ cells total from a single spleen).

An alternative method to the use of PEG as the fusogen is 'electrofusion', where an electrical field is used to fuse the spleen cells with myelomas. Under optimal conditions it has been possible to increase the fusion frequency to $10^{-3}$-$10^{-4}$ (Schmitt et al. 1989) or $10^{-3}$ (van Duijn et al. 1989), around an 80-fold improvement on the traditional PEG method described above. The number of antigen-specific hybridomas as well as the total number of hybridomas was similarly increased by this method, the improvement being independent of the immunisation procedure, the antigen or the source of the lymphocytes. Hui et al. (1993) has analysed a number of publications where the PEG and electrofusion methods have been compared directly in the same experiment. They conclude that on the whole, the electrofusion procedure offers an improvement in the fusion rate, either measured by the number of HAT resistant or antibody producing clones generated. A further report indicates approximately a 10-fold improvement in fusion rates—utilising the electrofusion technique compared to the PEG method—across thirty-six experiments (Karsten et al. 1993). However the rate of success is not consistent across all laboratories, thus demonstrating that there is still scope for refinement in the methodology and it's reproducibility.

Despite an increase in the fusion rate achieved by methods such as those described above, a percentage of hybridomas secrete no antibody at all. This is not thought to be due to fusion of myelomas with T cells, as there is no evidence for the presence of myeloma×T-cell heterokaryons from viable hybrids (Kohler et al. 1977; Clark and Milstein 1981). Problems may be encountered after the plating of fused cells due to overgrowth of hybrid cells by macrophages, fibroblasts and P cells (van Mourik et al 1984). One approach to help overcome these issues is to enrich for immunoglobulin secreting spleen cells by methods such as density centrifugation (van Mourik and Zeijlemaker, 1986) before fusing with the myeloma cells.

By bringing the spleen cells displaying cell surface receptors to the antigen (used to immunise the mouse) in close proximity to the myeloma cell, the efficiency of the fusion can be increased still further without the need for the density separation step. This procedure improves the efficiency of the fusion in two ways. Firstly by reducing the relative number of unwanted fusions, that is fusions between myeloma cells and spleen derived cells that are not capable of secreting antibodies. Secondly by selectively fusing antigen secreting cells that present only cell-surface receptors that bind the antigen of interest (Lo et al. 1984; Tsong and Tomita, 1993). This has been achieved by creating a 'bridge' between these two cells taking advantage of the strong interaction between biotin and streptavidin (Yuan et al. 2000). Thus an avidin-antigen conjugate is generated which binds the cell-surface antibody receptors on the splenic lymphocytes. Biotinylation of the myeloma cell brings it into close proximity with the antigen recognising lymphocyte population through a strong interaction with the avidin-antigen conjugate. Thus increasing the chances of successfully fusing lymphocytes of interest with the immortalising myeloma cell line by PEG fusion (Reason et al. 1987).

An alternative method to the use of PEG for catalysing the fusion of bridged spleen with myeloma cells is the application of the electrofusion technique (Lo et al. 1984; Hewish and Werkmeister 1989; Conrad and Lo 1990; Werkmeister et al. 1991). A combination of both methods yielding fusion frequencies of as high as $10^{-2}$, or a 10-fold improved (Tomita and Tsong 1990) over the electrofusion method alone (van Duijn et al. 1989).

A further approach to increasing the fusion rate through bringing the cells into closer contact utilises Neuramidase to remove sialic acid from the cell membrane (Igarashi and Bando 1990). It is thought that the extracellular membranous sialic acid prevents close intercellular contact and hence the likelihood of PEG facilitated fusion. Indeed such treatment yielded approximately twice as many HAT resistant clones and eight-fold more antigen-specific clones over non-treated cells. Combinations of the above techniques may improve further the reliability and efficiency of the cell-fusion procedure. Other methods shown to increase the fusion efficiency by 10- to 50-fold include the adoptive transfer of spleen cells from immunised animals to X-irradiated syngenic recipients, followed by antigen boosting and culturing of spleen cells with the antigen prior to the fusion (Siraganian et al. 1983).

In addition to the low frequency of fusion that is achievable—even utilising many of the modified fusion techniques described above—there are other inherent limitations to this approach of immortalising β-lymphocytes. The fusion methods described above do not discriminate between the cell-cycle phase of either of the fusion partners. Thus fusions may occur between cells in mitosis or interphase. This can lead to a phenomenon known as premature chromosome condensation, or PCC (Westerwoudt, 1985) which, under some circumstances, can lead to the disruption of cell division.

A further factor that can influence the final success of the fusion is chromosome stability (Westerwoudt, 1986). Thus after fusion the new cell contains a full complement of chromosomes from both parent cells. This must be reduced to a normal complement of chromosomes for sustained growth. This inevitably requires a loss of the equivalent of one complement of chromosomes, which may include chromosomes harbouring the antibody expressing genes. It is estimated that approximately 50% of hybridomas that initially express antibody after successfully fusing, loose their ability to do so due to chromosome loss (Clark and Milstein 1981). Additionally hybridomas may not survive in the HAT selection media due to loss of the spleen derived HPRT gene, which is located on the X-chromosome (Taggart and Samloff 1982).

Even if the cell is able to successfully fuse and adopt a hybrid karyotype of chromosomes, hybridoma lines often display some degree of karyotipic instability. This is often the reason why seemingly stable hybridoma lines suddenly stop secreting antibodies. Thus the long-term karyotipc stability of any hybridoma line is an inherent characteristic of each hybrid and is a function—at least in part—of the process of integration of the two parental genomes (Westerwoudt, 1986). Freeze-thawing of cells has been used successfully to determine which lines are unstable, since this process results in the loss of antibody production in unstable lines (Pravtcheva and Ruddle, 1983).

Selection of Hybridomas

The selection of hybridomas utilises specific growth features of both the spleen and myeloma cells. Firstly, as discussed above, spleen cells are unable to grow in culture, thus unfused cells die. Myeloma cells defective in the enzyme hypoxanthinephosphoribosyltransferase (HPRT) were originally selected by Kohler and Milstein (1975) since they are unable to grow in medium containing hypoxanthine, aminopterin and thymidine (HAT medium). Since the aminopterin blocks the main pathway for DNA synthesis while the rescue pathway requires HPRT to utilise the exogenous hypoxanthine and thymidine. Thus myeloma cells die in HAT medium while the spleen cells provide the HPRT gene that enables growth of the hybridomas.

Although some improvements have been made to the precise experimental details, the fundamental method for immortalising β-lymphocytes through fusion with myelomas has remained unchanged since the description of the technique by Kohler and Milstein in 1975. One aspect of this invention presents a method that increases the efficiency of immortalisation to a theoretical 100%, while greatly simplifying the whole procedure; eliminating the fusion step through the use of inducible oncogene(s)/antisense expression or post-translational activation of oncogenes through the use of transgenic technologies.

SUMMARY OF THE INVENTION

Accordingly, the present invention provides a method for producing immortalised antibody-secreting cells, comprising:
(a) providing a transgenic animal having antibody-secreting cells capable of expressing one or more transgenes, wherein the antibody-secreting cells are in a non-immortalised state in the absence of a stimulus and are capable of changing to an immortalised state by means of the transgene or transgenes upon exposure of the cells to the stimulus;
(b) extracting the antibody-secreting cells from the animal; and
(c) exposing the antibody-secreting cells to the stimulus, thereby immortalising the antibody-secreting cells by means of the transgene or transgenes.

In a further aspect, the present invention provides a method for preparing a clonal population of immortalised cells which produce a monoclonal antibody, comprising:
(a) providing a transgenic animal having antibody-secreting cells capable of expressing one or more transgenes, wherein the antibody-secreting cells are in a non-immortalised state in the absence of a stimulus and are capable of changing to an immortalised state by means of the transgene or transgenes upon exposure of the cells to the stimulus;
(b) extracting the antibody-secreting cells from the animal;
(c) exposing the antibody-secreting cells to the stimulus, thereby immortalising the antibody-secreting cells by means of the transgene or transgenes;
(d) selecting an immortalised antibody-secreting cell which produces the antibody; and
(e) preparing the clonal population of immortalised cells from the immortalised antibody-secreting cell.

In a further aspect, the present invention provides a method for producing a monoclonal antibody, comprising producing a population of immortalised cells by a method as defined above, and producing the monoclonal antibody from the population of immortalised cells.

In a further aspect, the present invention provides a clonal population of immortalised antibody-secreting cells obtained by a method as defined above.

In a further aspect, the present invention provides a monoclonal antibody obtained by a method as defined above.

In a further aspect, the present invention provides an isolated, immortalised antibody-secreting cell derived from a transgenic animal, wherein the cell expresses one or more transgenes, the cell is capable of being maintained in an immortalised state by means of the transgene or transgenes in the presence of a stimulus, and the cell is capable of changing to a non-immortalised state in the absence of the stimulus.

In a further aspect, the present invention provides an isolated clonal population of immortalised antibody-secreting cells which produce a monoclonal antibody, comprising a population of immortalised antibody-secreting cells as defined above.

In a further aspect, the present invention provides use of a transgenic animal for producing immortalised antibody-secreting cells, wherein the transgenic animal has antibody-secreting cells capable of expressing one or more transgenes, and wherein the antibody-secreting cells are in a non-immortalised state in the absence of a stimulus and are capable of changing to an immortalised state by means of the transgene or transgenes upon exposure of the cells to the stimulus.

In a further aspect, the present invention provides use of a transgenic animal for producing an antibody, wherein the transgenic animal has antibody-secreting cells capable of expressing one or more transgenes, and the antibody-secreting cells are in a non-immortalised state in the absence of a stimulus and are capable of changing to an immortalised state by means of the transgene or transgenes upon exposure of the cells to the stimulus, and the transgenic animal is used to provide immortalised antibody-secreting cells capable of producing the antibody.

By "transgenic animal" it is meant any animal which has been genetically modified. Typically the transgenic animal is modified such that it comprises foreign genetic material. Preferably the animal is a germ-line transgenic animal, which comprises one or more transgenes permanently and stably incorporated into its genetic material, and is therefore capable of transmitting the transgenes to its progeny. Typically the foreign genetic material is present in substantially every diploid cell nucleus in such a transgenic animal. The transgene may be capable of being expressed in all or only in some cells in the animal, provided that it is capable of being expressed in at least some antibody-secreting cells.

However, the transgenic animal need not necessarily be a germ-line transgenic animal. In an alternative embodiment, the foreign genetic material may be introduced into somatic cells by a route such as transfection, liposome- or viral-mediated transfer (e.g. via adenovirus). In these embodiments the transgene may be capable of being expressed only in some cells in the animal, provided that it is capable of being expressed in antibody-secreting cells. In one embodiment, the transgene is introduced into the animal by means of a retroviral vector, preferably a retroviral vector which preferentially infects lymphocytes or B cells. In another embodiment, the transgene is introduced into antibody-secreting cells or their precursors in vitro, and the antibody-secreting cells are then introduced into the animal. The antibody-secreting cells may be derived from the animal to which they are reintroduced, or from a different animal. In one embodiment, a transgene is introduced in vitro into (pluripotent) haemopoietic stem cells, lymphoid stem cells or other B cell precursors. The transgenic antibody-secreting cell precursors are then introduced into the animal, in one embodiment by means of a bone marrow transplant. The animal may optionally be treated to remove its own antibody-secreting cells (for instance by irradiation) before implantation of the transgenic cells, in order to create a radiation-induced bone marrow chimera The expression of the transgene may be transient in this embodiment, provided that the transgene is introduced into the antibody-secreting cells of the animal before the antibody-secreting cells are extracted from the animal (and if the animal is immunised, before the animal is immunised), and provided that the antibody-secreting cells are capable of expressing the transgene for a sufficient time after extraction that a clonal population of immortalised cells can be produced from a single immortalised cell. Regardless of which of the above methods is followed, it is important in the present invention that the transgene is introduced into an animal in vivo (whether by creating a germline transgenic, by introducing a transgene into cells in vitro and then introducing the cells into an animal, or by viral transfer in vivo), thereby creating a transgenic animal, before removal of the cells from the animal. If necessary, the transgene may be reintroduced into the cells in vitro in order to maintain them in an immortalised state.

By "transgene", it is typically meant a foreign gene which has been introduced into the animal. The foreign gene may comprise a gene which leads to the expression of an antisense RNA or ribozyme. In some embodiments, the foreign gene may comprise a foreign, regulateable (inducible) promoter. The transgene may comprise a mutant gene under the control of a foreign constitutive or inducible promoter. However the term "transgene" is also intended to encompass a native (wild-type) gene expressed under the control of a foreign, inducible promoter. In one embodiment, the transgenic animal may be a promoter replacement transgenic, wherein the native promoter sequence of a suitable oncogene or tumour suppressor gene is replaced by a foreign, inducible promoter.

The stimulus may be any type of stimulus, provided that it is capable of initiating immortalisation of the antibody-secreting cells. An appropriate stimulus is typically selected according to the nature of the transgene(s) and according to how the transgene may be regulated. According to particular embodiments, the stimulus may be a change (increase or decrease) in the temperature to which the cells are exposed, or a chemical stimulus (such as the application or withdrawal of a drug, hormone, or other chemical entity). In one embodiment the chemical stimulus regulates the expression of a transgene through an inducible promoter sensitive to the chemical stimulus. In an alternative embodiment, the temperature change regulates the activity of a protein which promotes or inhibits immortalisation of the antibody-secreting cells. Typically, the stimulus is chosen such that the stimulus is not present under normal conditions in the animal, in order that the antibody-secreting cells remain in a non-immortalised state in the animal. For instance, where the stimulus is a temperature change which regulates the activity of an oncogenic protein, the oncogenic protein should be inactive at the normal body temperature of the animal. Where the stimulus is a hormone or drug, the hormone or drug should be substantially absent or present only at a sufficiently low level in the animal such that the antibody-secreting cells remain in a non-immortalised state in the animal.

The stimulus is preferably applied to the antibody-secreting cells after they have been extracted from the animal. However, in an alternative embodiment, the stimulus is applied to the antibody-secreting cells while they are still in the animal. In this embodiment, the stimulus is preferably applied after immunisation (if the animal is immunised). Such a method may result in the initiation of immortalisation of the antibody-secreting cells while they remain in the animal. The stimulus is then continued to be applied to the antibody-secreting cells after they are removed from the animal. In this embodiment, it is preferable to remove the antibody-secreting cells from the animal soon after immortalisation. In order to prevent unnecessary tumour growth and suffering in the animal, it may be necessary to sacrifice the animal soon after initiating immortalisation, unless the stimulus is removed before immortalisation of the antibody-secreting and other cells in the animal has proceeded too far.

In one embodiment, a product of a transgene in the antibody-secreting cells inhibits a tumour suppressor function in the cells. By "tumour suppressor function" it is meant any system or activity in the cells which inhibits immortalisation of the cells. A tumour suppressor function typically results from the activity of a tumour suppressor gene product, for instance the protein product of the p53 gene. The tumour suppressor function may be inhibited in various ways, such as by inhibiting the activity of the gene product or by inhibiting transcription or translation of the tumour suppressor gene.

The invention provides methods for the rapid immortalisation, isolation and cloning of antigen and epitope specific monoclonal antibody producing β-lymphocytes from relevant tissues or cells of immunised and non-immunised (naive) mice. Mice being utilised as the host of choice for the purposes of example only. The breadth of the invention is not limited to the utilisation of mice, indeed any animal host in which the methods described herein could be applied by those skilled in the art is encompassed by the invention.

Specifically the invention describes the use of a transgenic mouse expressing an immortalising oncogene(s) of choice under the control of either a tightly regulated promoter or an oncogene whose activity can itself be regulated by altering the cell culture temperature. Activation of the oncogene leading to the immortalisation of the relevant cells, specifically antibody secreting cells derived from tissues including but not limited to; spleen, circulating lymphocytes, lymph node, adenoid, bone marrow, tonsils and other tissues of the lymphatic system. The transgenic mouse thus yielding the above mentioned immortalised antibody secreting β-lymphocytes. A further aspect of the invention describes the enhancement of the ability of the oncogene to immortalise the cell of interest by simultaneous targeting of appropriate tumour suppressor gene function. This being achieved through either the expression of antisense or ribozymes targeting the tumour suppressor mRNA or by the expression of proteins which themselves target the tumour suppressor protein leading to inactivation or increased rates of tumour suppressor protein degradation. In a further embodiment this is achieved through the use of transgenic mice in which a tumour suppressor gene has already been ablated. Such a transgenic mouse is then crossed with those described herein in which oncogenes can be activated by the intervention of the investigator.

A further aspect of the invention provides methods—including but not limited to fluorescence-activated cell sorting or dipole magnetic flow sorting—for the rapid selection and isolation of such immortalised antibody-secreting lymphocytes. Furthermore methods for isolating antibody secreting cells with multiple epitope specificities, all derived from a single animal immunised with one or more antigens are described. A further aspect of this embodiment being the use of cells harvested from a naïve mouse (one which has not been immunised) to identify those with pre-determined specificity(ies) for the antigen(s) of interest. Additionally the pooling of 'naïve' cells from several animals and the freezing down of aliquots of these cells for antigen recognition selection at a time subsequent to the harvest of those cells is presented as a further embodiment. A further aspect of the invention provides for methods to produce antibodies in mice with sequence and immunogenic characteristics of non-murine antibodies. A preferred embodiment of this being the production of humanised antibodies such that after appropriate selection and purification, the antibody could be used for therapeutic applications or the gene extracted through standard molecular biology methods and then expressed as a whole, or in fragments, in a host of choice.

DETAILED DESCRIPTION OF SPECIFIC EMBODIMENTS

Generation of Immortalised Lines of β-Lymphocytes Secreting the Antibody of Interest An alternative strategy to that of hybridoma production via the Kohler and Milstein (1975) methodology (see above) is to provide—within the β-lymphocyte harvested from the spleen (or other tissue) of the immunised mouse—the necessary genetic material to enable immortalisation to be induced through the alteration of specific environmental conditions. In this invention the provision of this genetic material is achieved through the use of transgenic technology (Ryding et al. 2001), thus ensuring that all progeny are homozygous for the modified chromosomal DNA. There are other methods of transferring genetic material to the chromosomal DNA including lipotransfection and viral delivery amongst others. However none of these methods can guarantee that 100% of the targeted cells will contain the genetic material of interest as can be with germline transmission in transgenic animals. Thus it is necessary to define two characteristics of the transgenic animal that are required for the purposes of the invention described herein.

Firstly a gene or combination of genes must be selected that when transcribed and/or in someway activated or deactivated, express a gene products(s) or antisense RNA molecule that will activate or deactivate specific signalling pathways in the β-lymphocyte leading to immortalisation of said cell. Secondly it is necessary to express or initiate and sustain activation of the required gene(s), gene product(s) or antisense RNA in a regulateable manner. It is crucial that expression and/or activation of these gene product(s) and antisense RNA can be tightly regulated both when the tissue or cells of interest are in situ in the animal and post-harvesting. Thus conferring on the cell the ability to grow both normally while in situ in the animal and indefinitely in culture—while continuing to secrete the antibody of interest during this time.

In this invention the most preferred embodiment involves the removal of either tissues containing β-lymphocytes (e.g. spleen, tonsil, lymph node, adenoid, appendix, peyer's patches, bronchial-associated lymphoid, mucosa-associated lymphoid tissue, bone marrow or any combination of the aforementioned cells or tissue types) or the harvesting of circulating β-lymphocytes and their subsequent immortalisation by the approaches described above.

Gene Products which May be Used to Immortalise the β-Lymphocytes

Genes which when activated lead to the unnatural immortalisation of a particular cell type are often referred to as oncogenes. Their activation is often linked with cancers and as such are associated with tumourogenesis. There are many cases where the molecular basis of a particular cancer has been linked—at least in part—to the inappropriate activation, or in some other way, regulation of an oncogene. Of particular note with respect to this invention are oncogenes associated with cancers of the immune system. More specifically cancers of β-lymphocytes and the identification of the genes involved in their tumourogeneis. The anomalous activation, or deactivation of such genes is often the result of abnormal chromosomal translocations where the normal transcriptional regulation of the oncogene is modified. Such is the case with the oncogene c-myc.

The translocation of c-myc into the IgH3 or L chain locus results in it's activation which is thought to be the molecular basis of Burkitt's lymphomas in Humans (Klein, 1981; Adams and Cory 1985; Gauwerky et al. 1988), plasmacytomas in mice (Stanton et al. 1983) and immunocytomas in rats (Klein 1988). The Ly-1 murine B cell, which is often found associated with neoplastic B cell diseases, is characterised by a 10-45-fold elevation of steady-state myc RNA levels and a 2-10-fold amplification of the c-myc locus. The increased c-myc expression is thought to contribute to the cell line's ability to grow immortally in vitro and for it's predilection for malignant transformation in vivo (Citri et al. 1987). The role of activated c-myc in the molecular basis of these lymphomas has been further demonstrated through the application of transgenic and yeast artificial chromosome technologies. Thus mice were generated in which a copy of the c-myc gene coupled to the core region of the human IgH heavy chain locus had been stably integrated into the genome (Palomo et al. 1999). The tumourogenic cells displayed a phenotype characteristic of β-cell lymphoblasts. These transgenic mice developed tumours of the abdomen, head and chest in addition to the spleen. Similarly, transgenic rabbits have been engineered to express c-myc under the control of the $Ig_\kappa$-chain enhancer (Sethupathi et al. 1994). Some of the tumours that developed from these rabbits were diagnosed as lymphomas of β-lymphoid lineage and could be maintained in vitro. Evidence of the potential interchangeability of the functions of c-myc and N-myc are demonstrated in transgenic mice, where c-myc has been replaced with N-myc (Nalynn et al. 2000). In these mice the growth and differentiation function of c-myc (when silenced) can be rescued by expression of N-myc. Transgenic mice expressing N-myc under the control of the immunoglobulin heavy chain enhancer ($E_\mu$) yield clonal β lymphoid tumours (Rosenbaum et al. 1989). Clonality suggesting that further genetic abnormalities may be required before immortalisation can occur. One genetic candidate is the p53 gene. Thus after reimplantation into C57BL6 mice, bone marrow cells derived from p53-null-/- mice (Jacks et al. 1994) infected with a myc expressing virus yield B lymphomas which are genetically polyclonal as determined by PCR analyses of the Ig gene DJ region (Yu and Thomas-Tikhonenko 2002). Indicating that only two genetic events are required to immortalise this cell type; in this specific case ablation of p53 activity and activation of myc.

The wider ability of the product of the myc gene to immortalise other cells, in this case dorsal root ganglion (DRG) cells by v-myc, has been demonstrated by Rayrnon et al. (1999). In these experiments a primary culture of human embryonic dorsal root ganglion cells has been immortalised by infection with a retroviral vector expressing v-myc under the control of the tetracycline-sensitive transactivator. Clonal lines could be isolated by limiting dilution and then maintained in culture as immortalised cell lines. The ability of these immortalised lines to redifferentiate into capsaicin sensitive DRGs after addition of tetracycline to the medium (addition of tetracycline inactivates v-myc transcription) was maintained for at least 65-doublings of the clonal line. That c-myc expression does not lead—at least in part—to loss of the pre-tumourogenic phenotype is exemplified by the fact that β-cell derived tumours induced by activation of c-myc maintain surface IgM expression (Kovalchuk et al. 2000).

Germline transgenic expression of v-abl under the control of the $E_\mu$ immunoglobulin heavy chain enhancer yielded three transgenic lines with a predisposition to develop clonal plasmacytomas secreting either IgA or IgG (Rosenbaum et al. 1990). Most of these plasmacytomas bore a rearranged c-myc gene, apparently as a result of spontaneous translocation to the IgH locus. Progeny of a cross with an analogous $E_\mu$-myc mouse yielded mice which rapidly developed oligoclonal plasmacytomas, but not pre-β lymphomas. This is most likely due to the fact that the heavy chain enhancer is not active in pre-B cells. Transformation of B cells with abl may also be facilitated through concomitant heterozygosity (+/−) at the Ink4a/Arf tumour suppressor locus (Mostecki et al. 2000).

The combined expression of v-abl with N-myc (Sugiyama 1994) or c-myc (Spieker-Polet et al. 1995) is a powerful approach to generating plasmacytoma lines. Indeed Spieker-Polet et al. (1995) have selected a HAT sensitive plasmacytoma line from transgenic rabbits expressing v-abl and N-myc under the control of the $E_\mu$ enhancer (Rosenbaum et al. 1990) and the κ-chain enhancer ($E_\kappa$; Sethupathi et al. 1994) respectively. The rationale behind generating this line was to provide a fusion partner in order to generate monoclonal antibodies through fusion with spleen cells derived from non-transgenic immunised rabbits.

Cell lines immortalised with the SV40 large T antigen have been generated using several approaches. The SV40 virus has been used to infect both spleen and bone marrow cells harvested from a rabbit hyperimmunized through intravenous injection with a pneumococcal vaccine (Collins et al. 1974). A cell line (TRSC-1) was isolated from a small focus of cells observed growing on the surface of one infected spleen-cell culture. The TRSC-1 cells expressed the SV40 large-T antigen and appeared to secrete a monoclonal antibody (as determined by isoelectric focusing) and this antibody specifically recognised a component of the pneumococcal vaccine (Strosberg et al. 1974). One of the mechanisms by which the Large T antigen may lead to cellular immortalisation is it's binding to and inactivation of the tumour suppressor protein p53 (Pipas and Levine 2001).

More specifically the gene for the Large T antigen may be transfected into a cell to generate an immortalised line (Katakura et al. 1998). A further extension of this approach has been to express the SV40 large T antigen under the control of a tissue specific promoter. Windle et al. (1990) describes the generation of anterior pituitary tumours in mice by expressing the large T antigen under the control of the human glycoprotein hormone alpha-subunit gene promoter/enhancer.

An SV40 mutant, which carries a gene expressing a heat-labile Large T antigen (tsA58), has been used to generate cell lines generated from rat embryo fibroblasts (Jat and Sharp, 1989), a human fibroblast cell line (Radna et al. 1989) and a rodent hepatocyte cell line through infection of mouse hepatocytes with the mutant virus (Lee et al. 1995). These cells can be grown as immortal lines at the permissive temperature of 33-35° C., but at 37-39° C. are unable to proliferate, due to the loss of function of the heat labile large T antigen.

The utility of this heat labile large T antigen has been taken one stage further through the generation of a transgenic mouse called 'Immortomouse' (Jat et al. 1991; Noble et al. 1995; Jat et al. (1997) U.S. Pat. No. 5,688,692; Jat et al. (1999) U.S. Pat. No. 5,866,759). In the Immortomouse, the large T antigen tsA58 gene is expressed widely under the control of the constitutive mouse major histocompatability complex H-2K$^b$ class I promoter (Weiss et al. 1983). This promoter can be further activated in the presence of interferon-gamma. The objective of generating such a transgenic animal was to provide a source of immortalised cells form potentially any tissue that could be harvested from the animal. Although not all source tissues have been tested there are many examples in the literature where this procedure has been successful (Noble et al. 1995). Cells which have been successfully immortalised using this system include; fibroblasts and cytokeratin$^+$ thymic epithelial cells (Jat et al. 1991) kidney collecting tubules (Takacs-Jarrett et al. 1998), hair cochlear (Jagger et al. 1999; Jagger et al. 2000), CA1 hippocampal (Virley et al. 1999), brain capillary endothelial (Kanda et al. 2000), bone marrow derived mesenchymal cells (Dennis and Caplan, 1996), hepatocytes (Lee et al. 1995; Allen et al. 2000), bone marrow (Chambers et al. 1993; Matsumoto et al. 1995; Liu et al. 1998) intestinal epithelial (Tavelin et al. 1999; Whitehead et al. 1993) skin fibroblasts, panceratic, astrocytes, neuronal cortical, endothelial, colonic epithelial and myoblast cells (Jat et al. (1997) U.S. Pat. No. 5,688,692).

Although the above technology has been in the literature for ten years, the prior art does not teach or suggest the derivation of immortalised β-lymphocytes from an 'Immortomouse' for the purpose of directly deriving monoclonal antibody producing clonal cell lines as envisaged in one embodiment of this invention.

Some cell lines—such as adult human mammary fibroblasts and epithelial cells—cannot be immortalised with the SV40 large T antigen alone. In these cases co-transformation with telomerase enables growth of the immortalised cell line (O-Hare et al. 2001). Immortalisation of human plasma cell lines secreting IgGs has been described by Kanki and Takeuchi (1995). This was achieved by transfecting cells with a plasmid expressing the SV40 large T antigen prior to conventional fusion with partner cells, preferably of human origin.

Immortalisation of β-lymphocytes can also be achieved by infection with Epstein-Barr virus (EBV). The EBV appears to exploit the normal program of cell cycle activation upon infection (Hollyoake et al. 1995). Specifically Cannell et al. (1996) have determined that the cell cycle protein pRb (retinoblastoma) is hyperphosphorylated upon EBV immortalisation of β-lymphocytes. More specifically nuclear antigen 2 (EBNA2) of EBV has been used to induce tumours in transgenic mice expressing EBNA2 under the control of the SV40 early enhancer/promoter and the EBNA2 promoter (Tornell et al. 1996). The use of the specific immortalising factor, be it EBNA2 or a combination of EBV derived proteins could be used to immortalise β-lymphocytes.

A systematic evaluation of which combinations of p53, v-abl, bcl2 and ras oncogenes and tumour suppressors could act co-operatively to immortalise β-lymphocytes cells was performed by Kumar et al. (1999). They found that v-abl/bcl2 was the only combination that successfully immortalised splenic β cells. Overell et al. (1989) describes the use of a retrovirus expressing v-Ha-ras and v-mycMC29 to immortalise β-lymphocytes. In this case they found that primary pre-β cells were preferentially immortalised over mature β cells. Further oncogenes or tumour suppressor gene deactivators, which are involved in the progression and maintenance of some β-cell tumours and thus may be considered for use as immortalising genes in this invention, include; v-rel (Zhang 1995), bcl-2 (Adams et al. 1999) a bcr-v-abl chimera (Hariharan et al. 1989; Harris et al. 1990), SV40 large T, papillomaviruses E6 and E7, adenovirus E1A, human T-cell leukemia virus, herpesvirus saimiri, p53 (Katakura et al. 1998), PIM1, RhoH/TTF (ARHH), PAX5 (Pasqualucci et al. 2001), mdm2 (Haupt et al. 1997; Kubbutat et al. 1997; Xirodimas et al. 2001). This list is given to indicate the preferred embodiments of the present invention; further oncogenes/tumour suppressor deactivators could be selected by those skilled in the art. The nature of the transgene is not particularly limited, provided that the method involves the application of regulated oncogene/tumour suppressor deactivator expression to yield immortalised β lymphocytes and subsequently the production of cell lines secreting the desired monoclonal antibodies.

Activation of Pathways which may Lead to Immortalisation of the Cell

A further method of β-lymphocyte immortalisation is to trigger appropriate signalling pathways, which upon activation result in immortalisation of said cell. In one example of this the phenomenon of synergy between an anti-CD40 mAb and Epstein-Barr virus (EBV) in the activation and transformation of human β-lymphocytes could be utilised (Tsuchiyama et al. 1997; Niedbala and Stott 1998; Rush and Hodgkin 2001). Exposure to anti-CD40 antibodies sensitises the β-lymphocytes and can improve prospects of immortalising the cell with EBV. Thus simultaneous ligation of the CD40 and CD21 complex (receptor for EBV) enhances both the short-term proliferation and the long-term transformation rates of human β-lymphocytes. Alternatively, elucidation of the intracellular-basis of the molecular mechanism underlying this synergy could provide a strategy for immortalising transgene expression.

Deactivation of Pathways which may Lead to Immortalisation of the Cell

In addition to oncogenes, whose upregulation may lead to tumourogenesis and cell immortalisation, there are also tumour suppressor proteins whose activity—in the main— have the opposite phenotypic effect to the oncogenes thus suppressing tumourogenic growth of cells. The balance of the activity of these two classes of proteins being key to the maintenance of desired cell growth characteristics. Thus it follows that deactivation of such suppressor proteins may lead either to immortalisation of a given cell, or increase the likelihood of achieving immortalisation through the simultaneous over expression/activation of oncogenes. Indeed this is the case (Mostecki et al. 2000; Yu and Thomas-Tikhonenko 2002). Deactivation may be achieved, principally, by one of two routes. Firstly by the expression of proteins which themselves deactivate or mediate the deactivation of the tumour suppressor or by the appropriate transcription or application of antisense mRNA/ribozymes or oligonucleotides targeting the sequence encoding the tumour suppressor gene.

The expression of the SV40 large T antigen may lead to the immortalisation of cell lines, including antibody-secreting cells derived from spleen (Collins et al. 1974; Strosberg et al. 1974). One of the mechanisms by which the Large T antigen may lead to cellular immortalisation is its binding to, and inactivation of, the tumour suppressor protein p53 (Pipas and Levine 2001). A further protein whose expression can lead to the inactivation of p53 is murine double minute-2 (mdm2). The mdm2 oncoprotein binds the transcriptional activation domain of p53 and prevents it from regulating target promoters in order to effect it's antiproliferative role (Symonds et al. 1993; Haupt et al. 1997). A further function of mdm2 is to target p53 ubiquitination leading to degradation in the proteasome (Kubbutat et al. 1997; Maki and Howley 1997; Fuchs et al. 1998; Xirodimas et al. 2001). The short half-life (30-60 minutes) of p53 (Maki and Howley et al. 1997) makes it an ideal candidate to target when rapid and synchronised immortalisation is desired.

Using a retroviral library expressing random p53 antisense sequences, specific sequences were identified which were highly effective at inhibiting translation of p53 mRNA in mouse embryo fibroblasts (Carnero et al. 2000). The reduction in p53 leading to an increased ability of these fibroblasts to survive in culture through passages at which the WT cells would normally undergo cellular senescence. Several other studies have utilised and validated the use of antisense to p53 in the study of it's role in cellular proliferation (Ferreira and Kosik 1996; Matsushita et al. 2000; Arora and Iversen 2000; Zhu et al. 2002; Shih et al. 2002), indicating that such an approach is well validated for the reduction of p53 activity in cell-based assays.

That p53 activity is not critical to whole animal viability has been demonstrated by the creation of a viable p53 knockout mouse (Jacks et al. 1994). Although viable, as expected this mouse is highly susceptible to malignancy. Yu and Thomas-Tikhonenko (2002) have taken bone marrow cells from this p53−/− transgenic and infected them with a myc expressing virus. The cells were then injected subcutaneously into C57BL6 mice. All mice injected with p53−/− derived myc infected cells developed tumours, while controls, which had not been myc infected, showed no sign of tumourogenic growth. Histopathological staining of the excised tumours indicated that all were β-lymphocyte lymphomas. Furthermore genetic analysis by PCR of the DJ junctions of the Ig gene showed multiple fragments, indicating that the tumours were polyclonal in nature. This result suggesting that loss of p53 activity and gain of myc activity are all that is required to induce tumourogenic and hence immortalised growth, specifically in β lymphocytes. Whereas clonality, which can be seen when myc alone is overexpressed in B cells (Langdon et al. 1986; Pelicci et al. 1986), would have suggested that further genetic modifications were required to induce a tumourogenic phenotype. Thus for the purpose of the invention described herein, ablation of p53 activity through the use of knockout mice, antisense p53 or mdm2 expression, combined with the expression of specific oncogenes under the control of inducible promoters in a transgenic animal, may, if used in the context of the detailed description herein yield immortalised cells secreting antibody of the desired specificity.

The targeting of the p53 tumour suppressor is given by way of example only, although p53 is used in a particularly preferred embodiment of the present invention. However it would be obvious to those skilled in the art that targeting of alternative tumour suppressor proteins/genes or regulators of tumour suppressor proteins/genes may also yield the desired cellular phenotype required for the purposes of the invention described herein. By way of example a further tumour suppressor gene that could be targeted is p16$^{Ink4a}$ (Sharpless et al. 2001; Mostecki et al. 2000).

Methods to Regulate Expression of β-Lymphocyte Immortalising Genes, Proteins or Antisense RNA Several genes or genes to be targeted using antisense RNA have been outlined above whose products—either upon expression, activation or deactivation—may lead to the immortalisation of the cell in which they are expressed. In the case of this invention the cell type of specific interest for immortalisation being antibody secreting β-lymphocytes. In the case of gene products whose activation may lead to cell immortalisation, there are two alternative methods of activating these immortalising factors. These may be classified as follows. Firstly activation through control at the level of gene transcription and secondly control of gene product activation. Control at the gene transcription level can also be used to regulate the transcription of antisense RNA/ribozymes in addition to the expression of immortalising proteins.

In essence, so long as cell immortalisation can be activated in β-lymphocytes post-harvest from the mouse and conversely be switched off pre-harvest, then the choice between these two control mechanisms is not a critical one. The key requirement to the approach chosen being that the maintenance of a wild-type cell proliferation control system in the mouse is achieved up to the point of β-lymphocyte harvest and the requirement for immortalisation. After which it should then be possible to immortalise the cells such that the pool from which β-lymphocytes can be selected and grown is fully representative of the cell diversity present in the tissue/cell-type of origin prior to sacrifice of the animal. Furthermore, that upon immortalisation these cells continue to secrete the antibody of interest, and preferably also present cell-surface receptors to the same antigen.

Control of Cell Immortalisation at the Transcriptional Level

The desired features of a system in which activation of cell immortalisation is dependent on control at the transcriptional/translational levels are as follows. The method of activation must be tightly regulated (no 'leakage'), such that cell proliferation mechanisms are functioning normally until immortalisation is desired. That activation of cell immortalisation is sufficiently rapid to ensure the cells of interest all enter the immortalised state within a short space of time and preferably simultaneously. That the activating factor, or for that matter the immortalisation factor itself, does not in any way interfere with the continued secretion of a single clone of antibody from the β-lymphocytes. Furthermore that the activator, or method of activation does not in any other way compromise cellular physiological processes whose targeting is not required for cell immortalisation. That the immortalisation can be either constitutively activated by the addition of the activator, or that the source of activator is available in sufficient quantities to support immortalised growth of all the clonal lines selected (Pollock and Rivera 1999; Wang et al. 1999).

In order to fulfil many of the requirements listed above it may be preferable to use a promoter system not usually found in the particular tissue/cell type of interest, in this case β-lymphocytes. More preferably the promoter system may be one that is not found in the host species at all.

A number of inducible promoter systems have been characterised which would fulfil the criteria outlined above. Several systems and techniques for conditionally expressing gene products in animals are discussed by Ryding et al. (2001). By way of examples only the control mechanism and characteristics of the following promoter systems will be described; tetracycline, GAL4, the ecdysone and the FK506-binding protein inducible expression systems. Although it is recognised that other similar systems are currently available and may become available and developed by those skilled in the art. It is not the specific promoter system employed that is crucial to the invention but the use of such systems to generate immortalised β-lymphocyte lineage's from transgenic animals coupled with the requirement for tight, 'non-leaky' regulation of the promoter which is critical. Although it should be noted that absolute control of over promoter 'leakiness' is not necessarily crucial, although highly preferable.

In the tetracycline regulated expression system (Brent et al. (1989) U.S. Pat. No. 4,833,080) two tetracycline operator sequences (tet-O) have been inserted between the TATA box of the strong CMV (Cytomegalovirus) eukaryotic promoter and the transcriptional start site. These sequences have no direct effect on the CMV promoter. However CMV driven transcription—and hence expression—is blocked when the tetracycline repressor protein binds to these tet-O sites. However if tetracycline is added to the cell culture medium it can penetrate the cell and bind to the repressor protein, changing its conformation such that it is released from the tet-O sites. Hence expression is turned on. If the immortalising oncogene were under the control of such a CMV/tet promoter a further transgene expressing the tetracycline repressor protein would have to be co-expressed constitutively in all cells, or at least in those cells in which subsequent immortalisation was desired. The promoter used could also be the CMV promoter, but in this case it would not be under tet control.

Conceivably other promoters could be used to express the tet repressor protein as an alternative to CMV. Furthermore to those skilled in the art it is conceivable that other mammalian promoters (either regulateable or constitutively active) could be combined with the tet-O sites to produce alternative inducible expression systems. The tet promoter system has been used successfully to control liver-specific expression of the SV40 large T antigen (Manickan et al. 2001). Expression of the large T antigen resulted in the development of hepatocellular adenomas and hyperplasia.

A further inducible expression system that can present tighter regulation than the tetracycline method described above is the Gal4 GeneSwitch. In this procedure the oncogene would be under the transcriptional control of a hybrid GAL4 UAS/E1b promoter, consisting of a 10-base pair TATA box sequence from the Adenovirus E1b gene and six binding sites for the yeast GAL4 protein. This promoter is transcriptionally silent in the absence of the GeneSwitch transactivator. The transactivator consists of three functional domains: a GAL4 DNA binding domain (to bind the GAL4 UAS/E1b promoter), human progesterone receptor ligand binding domain (hPR-LBD, binds the inducing agent mifepristone) and an NFκB p65 activation domain (to activate transcription off the GAL4UAS/E1b minimal promoter). In the absence of mifepristone, the hPR-LBD has a conformation which prevents the GeneSwitch protein from activating transcription. Upon binding mifepristone, HPR-LBD assumes a conformation that enables it to bind the promoter and stimulate transcription. The expression of the GeneSwitch protein itself is under the control of a minimally active TK promoter with four upstream GAL4 binding sites. Binding of the mifepristone activated GeneSwitch protein to this promoter results in further expression of the GeneSwitch itself, ultimately resulting in positive feedback enhancement of oncogene expression.

A further 'gene switch' mechanism again exploits the modular nature of eukaryotic transcription factors—that they can be divided into separable DNA-binding and transcriptional activation domains. These domains are able to reconstitute a sequence-specific transcriptional activator even when brought together through a noncovalent interaction (Spencer 1996). Thus fusion of each of these transcription factor domains (DNA-binding and transcriptional activating) to a heterologous ligand-binding domain enables reconstitution of an active transcription factor in response to the addition of cell-permeant dimeric ligands (Rivera et al. 1996; Pollock and Rivera 1999).

A derivative of the natural product FK506 binds with high-affinity to the FK506-binding protein (FKBP)-12 (Schreiber 1991), while the molecule FK1012—which consists of two covalently joined FK506 molecules—is able to dimerize two FKBP domains. This molecule (FK1012) has been used successfully to activate gene-transcription in a dose-dependent manner in cells expressing the appropriate reporter gene in addition to DNA-binding domain-FKBP and activation domain-FKBP fusion proteins (Ho et al. 1996). A modified form of FK1012 has been developed (AP1510) which is comprised of linked monomers of only the FKBP-binding interface of FK506 (Amara et al. 1997). However one drawback of AP1510 has been that it interacts with wild-type FKB protein.

A number of refinements to the FKBP transcription-activation system have been made to generate a gene-switch which—in the main—meets the criteria required as outlined above (Pollock and Rivera 1999). Alternative transcription factor domains used (ZFHD1) have a sequence-specificity distinct from that of known mammalian transcription factors (Pomerantz et al. 1995), thus avoiding inappropriate regulation of target expression by endogenous DNA-binding proteins. The FKBP protein and AP1510 have been modified such that the new ligand series (AP1889) may only bind a modified FKBP (FKBP$_{F36V}$) protein and not the unmodified FKBP (Clackson et al. 1998). Location of the ZFHD1 binding sites upstream of a minimal promoter such as those derived from the human interleukin-2 (IL-2), cytomegalovirus (CMV) and SV40 early gene generates promoters which may be regulated using the above described system. Stronger promoters such as the CMV and SV40 promoters display significant basal activity in the absence of the activator, while the IL-2 promoter gave rise to very low levels of basal expression with high levels of dimerizer-induced expression (Pollock and Rivera 1999).

A further gene-switch with modular DNA binding and activation domains utilises a C-terminally truncated human progesterone receptor lacking progesterone binding activity, but with the ability to bind the progesterone antagonist antiprogestin (RU486; Wang et al. 1999). A fusion protein consisting of (from the N-terminus) a domain from the herpes simplex viral protein VP16, a GAL4 DNA-binding domain (as described above) followed by the truncated RU486 responsive receptor forms the hybrid transcription regulator. Expression of this fusion protein in HepG2 cells was driven by the constitutive transthyretin enhancer/promoter. Four copies of the GAL4 binding domain upstream of a minimal E1B promoter driving expression of human growth hormone was also present on the same stably integrated plasmid, thus yielding a fully inducible expression system for human growth hormone (Wang et al. 1997b). Induction levels of 120-fold were achieved with 10 nM of RU486 with concomitantly very low basal levels of expression in the absence of the RU486 inducer. The successful application of this inducible expression system in transgenic mice has also been demonstrated. Thus Wang et al. (1997a) have measured a 1,500-fold induction of hGH expression in serum after administration of 250 ug/kg of RU486.

The ecdysone inducible expression system has two major advantages over the previous expression systems described (Saez et al. 2000). Firstly the promoter is very tightly regulated; thus there is very little 'leakage' or promoter activity in the absence of the activator. Secondly the system is based on a Drosophila promoter and transcription factor pairing, as a consequence the system is 'closed' and there is no interaction with wild type promoter functions in eukaryotic cells. In transient expression experiments with CV-1 cells No et al. (1996) have reported up to a 1000-fold increase in reporter activity of a gene linked to a modified ecdysone-inducible promoter, compared to a 59-fold increase for a tetracycline inducible promoter. In addition, the basal activity of the ecdysone-inducible promoter was 20-fold lower than the tetracycline inducible promoter. In expression experiments utilising a HEK-293 stable cell line, activation of the hormone receptor by 1 uM of the inducer muristerone resulted in an expression induction of 100-fold after 3 hours, 1,000-fold after 8 hours and 20,000-fold after 20 hours. Coupled with a very low basal activity in the absence of the inducer, this system and others with similar performance profiles, provide ideal methods of activating oncogene expression in antibody secreting cells, for the purposes described in this invention.

Furthermore No et al. (1996) have demonstrated the utility of this system in transgenic mice through the use of ESHβ, a thymus-specific promoter driving the expression of the hormone receptor domains. They demonstrated induction of promoter activity through the treatment of the mice with 10 mg of muristerone. This resulted in a significant induction from the ecdysone-inducible promoter while low basal activity was observed both in the absence of the muristerone and in tissues where the ESHβ promoter is not active. Invitrogen Corporation provides this system in kit form (Catalogue numbers of various kit components K1001-01, K1001-02, K1001-03, K1002-01, K1002-02, K1002-03, K1003-01, K1003-02, K1003-03, K1004-01, K1005-01) and make available an alternative activator to Muristerone, Ponasterone A (Saez et al. 2000). This system utilises a heterodimer of the ecdysone receptor (VgEcR) and a mammalian retinoid receptor (RXR) that binds the ecdysone response element (E/GRE) in the presence of Ponasterone A, thus activating expression of the gene of interest. It is the use of this system to regulate oncogene expression and hence cell immortalisation in β lymphocytes which is presented herein for the purposes of example only.

This system has been used successfully to study the effect of the expression of a constitutively active form of MKK7 on HEK-29 cells (Wolter et al. 2001). Most importantly RT-PCR, immunoprecipitation, confocal microscopy and FACS analysis revealed no significant basal expression of the GFP-MKK7$_{3E}$ fusion protein in the absence of the activator (inducer). In a further example where Ponasterone A inducible expression of β-galactosidase activity was targeted to the mammary gland of a transgenic mouse, basal (no Ponasterone A administered) activity (as determined with fast red staining) was undetectable on histochemical slices taken from mammary tissue. While β-galactosidase activity was detected in similar tissue after administration of the activator to the animal (Albanese et al: 2000).

In a third example the ecdysone gene switch has been used to regulate the expression of a dominant negative c-jun mutant/GFP fusion protein GFP-TAM67 transfected into the HT1080 human fibrosarcoma cell line (Hennigan and Stambrook 2001). In this study very low basal expression of the GFP-TAM67 was detected in the absence of the activator Ponasterone A.

RheoGene Inc. has licensed patents relating to the use of the ecdysone gene-switch technology as described in U.S. Pat. No. 6,258,603 (Carlson et al. 2001), U.S. Pat. No. 6,245,531 (Hogness et. al. 2001) and U.S. Pat. No. 5,514,578 (Hogness et al. 1996). Although the general utility of these patents is described, the precise application as outlined in this invention has not been realised. Refinements of the ecdysone gene switch technology being developed by Rheogene (Karns et al. 2001) may provide improved expression systems, which may be applied to the invention described herein. Such improvements include; more potent expression induction ligands, even lower basal expression levels in the absence of the activator and the development of multiplex switching in which specifically engineered ecdysone promoters, receptors and RXR proteins may be activated with specific switch activators, called RheoChem/RheoReceptor pairs. Such a multiplexing option would enable the precise regulation of the expression levels of multiple oncogenes described in this invention for immortalising β cells. A further improvement to the switch system that enables higher levels of induction involves the co-ad-ministration of an RXR ligand, such as LG268, in addition to the EcR ligand Ponasterone A (Saez et al. 2000). The two ligands act synergistically resulting in a four-fold increase in the induction levels seen with Ponasterone A alone.

The inducible-promoter systems described above are intended as examples only. An investigator skilled in the art may identify, develop or devise similar inducible expression systems to selectively express the oncogene when required. Thus the invention is not limited to the use of one or more of the systems described above. Rather it is the immortalisation of every β-lymphocyte/antibody secreting lineage by either one of the above or some other method for the production of monoclonal antibodies that is the inventive step rather than the utilisation of any particular inducible expression system to express any particular oncogene or combination of oncogenes per se.

Control of Cell Immortalisation at the Protein Activation Level

As an alternative to controlling transcription of the gene product it may be expressed constitutively, but in a conditionally inactive form. An example of such a gene product that could be activated by the manipulation of external conditions is the temperature-sensitive Large T antigen (tsA58 described above). In the transgenic mouse, 'Immortomouse' (Jat et al. 1991; Noble etal. 1995; Jat et al. (1997) U.S. Pat. No. 5,688, 692; Jat et al. (1999) U.S. Pat. No. 5,866,759) the large T antigen tsA58 gene is expressed widely under the control of the constitutive mouse major histocompatability complex H-2K$^b$ class I promoter (Weiss et al 1983). This promoter can be further activated in the presence of interferon-gamma. Although not all source tissues have been tested there are many examples in the literature where this procedure has been successful in generating immortalised cell lines (Noble et al. 1995). See above for discussion of the utility of the 'Immortomouse' for providing immortalised cell lines.

Several other methods of (conditionally) immortalising the cell may be developed by those skilled in the art. The present invention is not limited to particular methods of immortalisation, provided that the method involves the application of such immortalisation approaches to the rapid isolation of specific antibody secreting β-cells and hence antibodies through the immortalisation of said β-cells.

Screening for Immortalised β-Lymphocyte Cells Secreting Antibody(ies) of the Required Specificity(ies)

Whichever method for immortalisation is selected they are all intended to yield a population of cells which are capable of clonal growth. The number of clones limited only by the number of cells harvested, likely to be the total number of spleen cells or cells harvested from other lymphoid tissue such as lymph nodes. This cell population will consist of both non-secreting (T-cells, macrophages etc) and antibody secreting cells. Of the antibody secreting cells only a proportion will be secreting—and in some cases also displaying on the cell-surface—antibodies recognising the antigen used to immunise the mouse. Thus a rapid screening method is required to select for the latter cell-type, whether or not the cell secreting an antibody of interest is also displaying cell-surface receptors which bind that antigen. This can be achieved utilising the technology of fluorescence activated cell sorting (FACS).

Hybridomas secreting a monoclonal antibody of interest and also displaying cell-surface immunoglobulins recognising this antigen have been selectively isolated using the FACS technique. This has been achieved by fluorescently labelling the antigen, mixing this with the hybridomas and sorting for cells which bind the antigen as determined by their altered fluorescent properties (Parks et al. 1979; Dangl and Herzenberg 1982; Jantscheff et al. 1993; Martel et al. 1988). A method has also been developed in which a FACS is used to sort hybridomas which secrete a monoclonal antibody but do not express cell-surface immunoglobulins specific for the antigen (Gray et al. 1995). Single hybridomas are captured within a microdroplet of biotinylated agarose. The addition of biotinylated and fluorescently labelled antigen and avidin to this droplet mixture resulting in the fluorescent labelling of microdroplets harbouring a single hybridoma, secreting antibody specific for the antigen. Specific droplet—hence hybridoma—labelling being achieved through the capture of the secreted antibody in the microdroplet via an antibody-antigen-avidin-biotinylated agarose bridge. In a further development of this technique, two-colour detection modes on the FACS have been utilised to select for cells secreting antibodies to unique epitopes (Kenney et al. 1995).

In this invention immortalised cells harvested from tissues of the lymphoid system including the lymph nodes or spleen, but not excluding other sources are sorted using a FACS or an instrument with similar cell-sorting capabilities by methods similar to those described above. However lymphocytes immortalised by methods described in this invention are selected rather than hybridomas generated via the conventional method of Kohler and Milstein (1975) as applied above. A wide selection of fluorescent markers are available to enable differential labelling of antigens and epitopes and hence detection and isolation of specific Ig secreting β-cells. Judicious selection of the appropriate labels for use in combination will depend on a number of factors including instrument excitation and emission wavelengths, dichroic mirror settings and other instrument parameters, including the ability to discriminate between the labels. The precise label used is not central to the invention but by way of example the following is a non-exhaustive list of fluorescent labels which may be utilised; hydroxycoumarin, aminocoumarin, methoxycoumarin, cascade blue, lucifer yellow, R-phycoerythin, Cy5, Cy7, Red 613, fluorescein, BODIPY-FL, Cy3, TRITC, X-rhodamine, Lissamine Rhodamine B, PerCP, Texas Red, allophycocyanin, TruRed, phycobiliproteins, green fluorescent protein (GFP) and the following GFP derivatives; Y66F, Y66H, EBFP, GFPuv, ECFP, Y66W, S65A, S65C, S65L, S65T, EGFP and EYFP. All of which may be conjugated to the antibody of choice via a variety of methods including but not exclusively; coupling via amine, sulphydryl or carboxyl groups utilising either homobifunctional or heterobifunctional linkers.

In a further embodiment of the invention, the initial harvest of β-lymphocytes from the immunised mouse could be subdivided, thus enabling the repeated use of a small subset of these lymphocytes for sorting. The subdivisions enabling the repeated use of the same fluorophores to sort for β-lymphocytes with different antigen specificity's. This would be achieved by labelling different antigens with the same fluorophore but selecting for cells specific for these antigens in separate runs on the FACS, using separate aliquots of β-lymphocytes harvested from the same mouse.

In a further embodiment of the invention β-lymphocytes could be harvested from a naïve (non-immunised) mouse (from which immortalised β lymphocytes may be derived by one of the approaches described above) and used directly to select for those presenting surface and/or secreted Igs that bind the antigen/epitope of interest.

In the simplest embodiment of the invention the mouse is immunised with a single antigen and cells expressing surface immunoglobulins or secreting immunoglobulins specific for that antigen are selected and immortalised. However it would be obvious to those skilled in the art that variations to this protocol could be utilised to generate further reagents. The following modifications are given by way of example only: immunising a mouse with multiple antigens and selecting cells with specificity's to each antigen, immunising with a single antigen and selecting for cells with multiple epitope specificity's on the same antigen, immunising with multiple antigens and selecting for cells with multiple epitope specificity's on each of those antigens.

A further embodiment relates to the freezing down of spleen cells (Marusich 1988; Bennick et al. 1991) from mice—either naïve or immunised with the antigen of interest—derived from similarly engineered mice (capable of yielding β-lymphocytes that may be immortalised employing one of the approaches described above). Thus such cells could be frozen in aliquots and FACS screens performed on them when required. In the case of the cells derived from the naïve mouse, screens could be performed against any antigen with theoretically a similar chance of successfully isolating the required clone. The technique could be more powerful if several 'naïve'spleens are harvested together and the total cell population mixed, then aliquoted in order to generate 'libraries' with maximum diversity.

Screening for Cells Displaying β-Lymphocyte Specific Cell-Surface Markers

In a further embodiment of the invention, utilisation of the dual or multi-detection capability of the FACS would enable selection for β-lymphocytes from the mixed cell population harvested from the mouse through the use of fluorescently labelled anti-β cell specific mAbs. Fluorescently labelled monoclonal or polyclonal antibodies specific for any—or a combination—of the following antigens may be utilised to selectively enrich for the appropriate β-lymphocyte population; B220, CD19, sIgM, sIgD, sIgG, CD23, CD19, CD40, CD79a, CD79b, MHC class II (Hardy et al. 1991; Allman et al. 1993; Erickson et al. 1996). This selection procedure may then be used in combination with any of the antigen specific procedures outlined above to further ensure that cell populations sorted are indeed of β-lymphocyte lineage.

Use of Alternative Instruments Other than the FACS to Sort the β Lymphocytes

An alternative cell-sorting system utilises a magnetic colloid, which when coupled to an antibody with a specificity to the cell of interest confers on it a magnetic label. The cells are then passed through a dipole magnetic flow sorter, which separates cells according to their magnetic properties, which are in turn defined by their interaction with the colloid-labelled antibody (Moore et al. 1998). This method has been used successfully to sort T lymphocyte subpopulations. Thus rather than label the antigen of interest with a fluorescent marker, as required for FACS sorting, the antigen would be labelled with the magnetic colloid. Thus immortalised β-lymphocytes secreting antibodies with the appropriate specificity, whether or not also expressing cell-surface immunoglobulins, could be labelled and hence selected.

Generation of Monoclonal Antibodies in Other Species

The host of choice for the production of monoclonal antibodies has remained the mouse since the origination of the technique by Kohler and Milstein (1975). However antibodies have also been produced in other species; most notably rats, rabbits and sheep. A rat myeloma line has been developed for rat-rat fusions (De Clercq et al. 1986). Spieker-Polet et al. (1995) describes the derivation of a fusion partner to enable the production of rabbit-rabbit hybridomas. The cell line was derived by the generation of a double transgenic expressing the v-abl oncogene under the control of the $E_\upsilon$ heavy chain enhancer (Rosenbaum et al. 1990) and the N-myc oncogene under the control of the Eκ κ-chain enhancer (Sugiyama 1994). A HAT sensitive fusion-partner was generated by appropriate selection of cells derived from the tumourous spleen after x-ray irradiation in the presence of 8-azaguanine. Methods for producing antibodies using cows (Guidry et al. 1986), sheep (Flynn et al. 1989), pigs (Lumanglas and Wang 1995) and hamsters (Sanchez-Madrid and Springer 1986) as hosts have also been described. These approaches utilised a method involving the formation of inter-species heterohybridomas between murine myelomas and spleen cells from the immunised host of choice. It is obvious to those skilled in the art that the invention described herein could be applied similarly to any of the above species and others in which the appropriate genetic technologies had been developed.

Generation of Humanised Antibodies

The successful application of mouse derived monoclonal antibodies for human therapeutic applications has been hindered due to the immunogenicity in man of the mouse antibody, independent of it's antigen specificity. Such human anti-mouse antibodies (HAMA) neutralise the administered antibody and can also lead to toxicity in the patient. Thus there is great potential for the production of humanised monoclonal antibodies, specifically for therapeutic applications. Several approaches have been taken to generate humanised monoclonal antibodies. These include EBV/electrofusion facilitated fusion of human blood-derived β cells with standard mouse myelomas (Foung and Perkins 1989; Foung et al. 1990) or SPAZ-4 (Ostberg 1986), SPAM-8 (Gustafsson et al. 1991; Panova and Gustafsson 1995), Hab-1 (Faller et al. 1990) or CBF7 (Grunow et al. 1990; Walper et al. 1990; Niedbala and Stott 1998) heteromyelomas. These heteromyelomas being IgG non-secreting human/mouse hybrids. Other methods have included exposure of human β-lymphocytes to anti-CD40 mAbs and EBV (Tsuchiyama et al. 1997; Niedbala and Stott 1998). Pure human fusion partners have also been established, including the HAT sensitive line HK-128 (Kawahara et al. 1990), established from a human plasmacytoma line and A4H12 cells (Kawahara et al. 1992).

Improved yields of human IgG-secreting hybrids have been achieved by in vitro priming the cultured lymphocytes with antigen prior to fusion (Boerner et al. 1991). A further improvement to the method for generating human lymphocyte-derived hybridomas involves the clonal expansion from single β-lymphocytes in the presence of human T cell supernatant and irradiated murine thymoma helper cells (Steenbalkers et al. 1992).

A further aspect of the invention describes the derivation of humanised antibodies utilising the antibody production technology described herein, but with a host transgenic animal in which the endogenous immunoglobulin genes have been replaced with human versions of the same genes. However the scope of the invention is not limited solely to providing humanised antibodies. It would be obvious to those skilled in the art that the mouse Ig loci or function thereof could be replaced with the Ig loci of other species. In this invention the production of humanised antibodies may be achieved by crossing the transgenic mice described herein with a transgenic line where the mouse Ig genes have been replaced with their human equivalent. Such a line is available in the form of the 'Xenomouse' developed by Abgenix and described by Kucherlapati et al. 2000 (U.S. Pat. No. 6,114,598). The 'Xenomouse' is presented by way of example as an established method. An extension of the Xenomouse technology is described in U.S. Pat. No. 6,207,418 (Hori et al. 2001). In this invention a method is described in which the genes coding for the innnunoglobulin heavy and light chains of β-lymphocytes harvested from immunised mice—including Xenomice—are cloned and expressed in separate cells. Cells expressing the heavy and light chains are then fused to generate cells expressing the functional antibody.

GenPharm international Inc. (now Medarex) developed a similar mouse technology (HuMab) which can be used for generating humanised monoclonal antibodies (Lonberg and Kay (1999) U.S. Pat. No. 5,877,397; Lonberg and Kay (1999) U.S. Pat. No. 5,874,299). Alternative methods are described for suppressing the endogenous Ig expression, including disrupting the endogenous Ig loci or the use of antisense polynucleotides or antiserum targeting either the endogenous Ig transcripts or protein respectively.

Two variations on the above approach are as follows. Firstly to use a different host species for the production of the humanised antibodies. Thus the immortalisation technology as described in this invention could be developed in any other species for which the appropriate transgenic technology was available, for example but not limited to rats, rabbits and sheep. Similarly the technology described in Kucherlapati et al. ((2000) U.S. Pat. No. 6,114,598) could also be developed in species such as rats, rabbit, and sheep. Thus crosses between identical and preferably isogenic species, each germline transgenic for each of the two technologies (described herein and in Kucherlapati et al. 2000), may yield offspring with similar utility as that described above.

EXAMPLES

Example 1

Derivation of Transgenic Mice Expressing the Ecdysone and RXR Receptors

Preparation of the VgEcR-RXR DNA Fragment

The region encoding the VgEcR and RXR genes, including the appropriate transcriptional and translational regulatory control elements (CMV promoter, VgEcR gene, TK polyadenylation signal, RSV promoter, RXR gene and the BGH polyadenylation signal) and 25 base pairs of vector sequence flanking both the 5' and 3' of these elements is PCR amplified from the Vector pVgRXR (Invitrogen; Cat#V730-20) using the following primers, 5'-GTACTAGTAGGGATTTTGGT-CATGGCTAG-3' (Sequence ID 1; 5' VgEcR-RXR primer) and 5'-GTACTAGTCAGCTGGTTCTTTCCGCCTCAG-3' (Sequence ID 2; 3' VgEcR-RXR primer). The primers include Spe I restriction site 'tails'. There are no other Spe I sites present in the amplified PCR product. The 6,134 bp PCR product is then digested with Spe I to yield a 6,124 bp product which is cloned into Spe I digested and dephosphorylated pcDNA2.1 (Invitrogen; Cat#V400-20). A positive clone (pcDNA2.1-VgEcR-RXR), containing a copy of the PCR product is then sequenced across the recombinant insert to confirm the fidelity of the PCR.

Preparation of the DNA Fragment for Injection into the Mouse Egg

A Qiagen maxiprep kit (Qiagen Cat#12362) is used to prepare >500 ug of pcDNA2.1-VgEcR-RXR plasmid DNA. A 300 ug aliquot of this DNA is digested with Spe I and the 6,124 bp insert (VgEcR-RXR) separated from the 2,981 bp fragment by gel electrophoresis and extracted using the Qiaquick gel extraction kit (Qiagen; Cat#28740). The extracted DNA is then brought to 10 ml in 1×TE buffer (10 mM Tris pH7.5/1 mM EDTA) and 10 g CsCl added and mixed gently to dissolve. The sample is loaded into an ultracentrifuge tube and centrifuged at 65,000 rpm for 6 hours in a vertical rotor at room temperature. Fractions (0.5 ml) are collected using a needle inserted approximately 1 cm from the bottom of the tube. Aliquots (5 ul) of each fraction are run on an agarose gel (1% in 1×TAE) and fractions containing DNA determined by exposure of the gel to u/v light. These DNA containing fractions are then pooled and dialyzed against 100× volume of microinjection buffer (5 mM Tris pH7.4/0.1 mM EDTA) for 8 hours. This dialysis is repeated a further three times. The concentration of the DNA is then determined by measuring the absorbance at 260 nm (microinjection buffer used to blank the spectrophotometer) of a 1:10 and 1:100 diluted (in microinjection buffer) sample of the dialysed DNA and by application of the formula: One unit of absorbance at 260 nm (path-length of 1 cm) of double-stranded DNA=50 ug/ml. A sample of the DNA is then prepared for microinjection by diluting to 2 ug/ml in microinjection buffer and sterile filtering through a 0.22 uM Millex-GV filter (Millipore; Catalogue #SLGV R25 LS).

Generation of a Homozgyous Transgenic Mouse Line for VREcR-RXR

Pro-nuclei of fertilized eggs derived from a CBA×C57BL/10 mating are microinjected with ~2 pl of the VgEcR-RXR insert purified above. The microinjected eggs are then transferred into pseudopregnant females (see method in Kollias et al., 1986) and the offspring analysed for the presence of the transgene in the genomic DNA as follows. Genomic DNA is prepared by phenol chloroform extraction and ethanol precipitation of 100 ul blood taken from 10 day old pups. Using the primers SEQ ID 16 and SEQ ID 2, PCR is performed on this genomic DNA and the presence of a 1,594 bp product used as an assay to indicate the presence of the transgene. Amplification of a fragment of the beta-globin gene (expected fragment size of 494 bp) is performed in parallel in each of the above reactions as a positive control using the primers 5'-CCAATCTGCTCACACAGGATA-GAGAGGGCAGG-3' (SEQ ID 11; 5' beta globin primer) and 5'-CCTTGAGGCTGTCCAAGTGATTCAGGCCATCG-3' (SEQ ID 12; 3' beta globin primer). Amplification conditions for the PCR reaction are 94° C. for 30 seconds, 60° C. for 90 seconds and 72° C. for 120 seconds repeated for 35 cycles with a final extension for 10 minutes at 72° C. Positive G0 (VgEcR-RXR positive) founders are back-crossed with the parents and the subsequent progeny (G1) similarly analysed by PCR. Male and female VgEcR-RXR positive mice are then crossed and samples of genomic DNA prepared and analysed as above until homozygous mice are identified (by comparing PCR product band intensities). These mice are then used as the founders of a homozygous continuous line of mice called VgEcR-RXR homozygotes.

Example 2

Derivation of Transgenic Mice Expressing c-myc Under the Control of the Ecdysone Inducible Expression System Preparation of the C-Myc DNA Fragment The coding sequence for c-myc (GenBank Accession number: X01023) is PCR amplified from a mouse spleen library (Clontech; Cat#7134-1) utilising the following PCR primers, 5'-GTAGCTAGCGCCACCATGCCCCT-CAACGTGAACTTC-3' (SEQ ID 3; 5' c-myc primer) and 5'-GATCTCGAGTTATGCACCAGAGTTTCGAAG-3' (SEQ ID 4; 3' c-myc primer). The 1,344 bp PCR product is then digested with Nhe I and Xho I, whose sites are engineered into the PCR primers and flank the coding sequence at the 5' and 3' respectively. The 5' primer also codes for a Kozak consensus sequence between the Nhe I site and the ATG initiation codon of c-myc. The 1,332 bp digested PCR product is cloned into the 4,934 bp gel-purified DNA fragment from an Nhe I and Xho I digestion of pIND (Invitrogen; Cat#V705-20) to generate a 6,266 bp product called pIND-c-myc. The insert of pIND-c-myc is confirmed by sequencing both strands of the cloned PCR product. The insert along with the appropriate expression control elements including the five hybrid E/GRE binding sites, the HSp promoter, a BGH polyA signal and 25 base pairs of vector sequence flanking the expression and control elements, are PCR amplified utilising the following primers 5'-GTACTAGTTGCCACCT-GACGTCGACGGATC-3' (SEQ ID 9; 5' pIND primer) and 5'-GTACTAGTCTCAGAAGCCATAGAGCCCAC-3' (SEQ ID 10; 3' pIND primer). The 2,124 bp PCR product is then digested with Spe I to yield a 2,114 bp product which is cloned into Spe I digested and dephosphorylated pcDNA2.1 (Invitrogen; Cat#V400-20) to yield a 5,085 bp construct called pcDNA2.1-IND-c-myc. The fidelity of the PCR is confirmed by double-stranded sequencing of the Spe I insert. Preparation of the DNA Fragment for Injection into the Mouse Egg and Generation of a Homozygous Transgenic Mouse Line Called IND-c-myc An aliquot of the Spe I insert is prepared for injection into fertilised mouse eggs as described in Example 1 (Preparation of the DNA fragment for injection into the mouse egg) except that in this case the Spe I fragment to be purified is 2,114 bp. The fertilized eggs are then injected with the IND-c-myc Spe I fragment and mice homozygous (called IND-c-myc homozygotes) for the integrated ID-c-myc are derived as described in Example 1 (Generation of a homozygous transgenic mouse line for VgEcR-RXR). Except that the presence of the insert in the blood derived genomic DNA preparation was confirmed utilising the primers 5'-ACAGCTTC-GAAACTCTGGTGC-3' (SEQ ID 13; 5' c-myc transgene confirmation primer) and SEQ ID 10 to yield an expected PCR product of 309 bp in replacement of primers SEQ ID 2 and 5'-CAGCTGCATTCTCCCATCAGC-3' (SEQ ID 16; 5' VgEcR-RXR transgene confirmation primer).

The IND-c-myc homozygotes described above are then crossed with VgEcR-RXR homozygotes described in Example 1 to yield a double homozygous line called VgEcR-RXR/IND-c-myc. After sacrifice by cervical dislocation, cells are harvested from VgEcR-RXR IND-c-myc mice from tissues of interest that contain antibody secreting cells such as spleen, tonsil, lymph node, adenoid, appenidix, peyer's patches, bronchial-associated lymphoid tissue, bone marrow, mucosa-associated lymphoid tissue or circulating β-lymphocytes. In general the spleen cells are harvested. Where required the cells are gently dissociated from the tissue using a 25 g needle and syringe and flushing with RPMI-1640 (Sigma; Cat#R0883). The cells are then split into four aliquots and placed in four separate 50 ml flasks (Greiner; Cat#690175). Two containing 10 ml RPMI-1640 with 2 mM glutamine (Life technologies; Cat#25030-024), 10% Foetal Bovine Serum (Life Technologies; Cat#16000-036) and 100 units Penicillin/100 ug Streptomycin per ml (Life technologies; Cat#15140-114). The other two flasks containing the same as above plus 5 uM Ponasterone A (Invitrogen; Cat#H101-01). Note, Muristerone A (Invitrogen; Cat#H100-01) may be used as an alternative to Ponasterone A. The four flasks are then incubated at 37° C./5% $CO_2$ for 24 hours. The cells are then harvested from one flask where cells were grown in the presence of Ponasterone A and one in which Ponasterone A was not present, using a cell scraper, 24 hours after plating. Cells were then washed and centrifuged (3,000× g) twice in 10 ml of PBS, before determining the protein concentration of the sample using the Bradford protein assay (Bio-Rad; Cat#500-0002). Different concentrations of cells (10 to 0.1 ug total protein) are separated by SDS-PAGE under reducing conditions and the protein transferred to nitrocellulose by standard Western blotting techniques. Using an anti-c-myc antibody (Santa Cruz biotechnology; Cat#sc-764) and standard Western blotting techniques known to those skilled in the art, the relative increase in c-myc expression in the cell sample incubated with the activator Ponasterone A is confirmed. That these cells—at least in part—include a population of immortalised β lymphocytes is determined by Western blotting, detecting with an antibody specific for such cells, for example anti-CD19 (Santa Cruz; Cat#8500). In addition immortalisation of the cells cultured in the presence of Ponasterone A and not those lacking Ponasterone A is demonstrated in that the former cells grow after repeated cell passage, whereas the latter cells die after a few days and thus cannot be indefinitely passaged. Thus demonstrating the utility of Ponasterone A regulateable c-myc expression for immortalising spleen cells.

Example 3

Derivation of Transgenic Mice Expressing abl Under the Control of the Ecdysone Inducible Expression System This procedure is identical to that described for deriving the c-myc transgenic described in Example 2 except for the following modifications. The coding sequence for abl (GenBank Accession number: V01541) is PCR amplified from a mouse spleen library derived from a mouse infected with the Abelson murine leukemia virus utilising the following PCR primers, 5'-GTAGCTAGCGCCACCATGGAGCCTGGTG-GAGTTGGC-3' (SEQ ID 5; 5' abl primer) and 5'-GATCTC-GAGTCAAGCTTGCTGTCCAAGATC-3' (SEQ ID 6; 3' abl primer). The 516 bp PCR product is then digested with Nhe I and Xho I and the 504 bp digested product is cloned into the 4,934 bp gel-purified fragment from an Nhe I and Xho I digestion of pIND (Invitrogen; Cat#V705-20) to generate a 5,438 bp plasmid called pIND-abl. The insert of pIND-abl is confirmed by sequencing both strands of the cloned PCR product. The insert along with the appropriate expression control elements are cloned into pcDNA2.1 as described in Example 2 except that the PCR product generated with primers SEQ ID 9 an 10 is 1,296 bp and 1,286 bp after Spe I digestion. This Spe I digested product is then cloned into Spe I linearised pcDNA2.1 to yield a 4,257 bp plasmid called pcDNA2.1-IND-abl. The homozygous double transgenic mouse line called VgEcR-RXR/IND-abl is then prepared similarly as that for c-myc described in Example 2 but in this example using the Spe I IND-abl fragment for mouse injections. Presence of the IND-abl insert in the blood genomic DNA sample is confirmed using the primers 5'-AGCTGC-CCTGCACCTTTCCTG-3' (SEQ ID 14; 5' abl transgene confirmation primer) and SEQ ID 10 to generate a PCR product of 733 bp. Induction of abl expression in the presence of Ponasterone A is demonstrated similarly to c-myc as described in Example 2, except that an anti-abl antibody (Santa Cruz; Cat #13076) is used to detect increased expression of abl upon induction. The ability to generate immortalised spleen cells with the VgEcR-RXR/IND-abl mouse line is demonstrated similarly to the method described in Example 2 for the VgEcR-RXR/IND-c-myc line.

Example 4

Derivation of Transgenic Mice Expressing abl and c-myc Under the Control of the Ecdysone Inducible Expression System The VgEcR-RXR/IND-c-myc transgenic mouse (see Example 2) and the VgEcR-RXR/IND-abl transgenic mouse (see Example 3) are crossed to yield a triple homozygous transgenic called VgEcR-RXR/IND-abl/c-myc. The presence of all three transgenes is confirmed using the following primer pairs to generate PCR products of defined size from genomic DNA samples derived from blood samples taken from the transgenic mice; SEQ ID 16 and 2, 13 and 10, and 14 and 10 for the confirmation of the presence of VgRXR (1,594 bp), IND-c-myc (309 bp) and IND-abl (733 bp) transgenes respectively. The primer pair SEQ ID 11 and 12, which amplifies a 494 bp beta globin gene product is used as a control in each of the above PCR reactions to confirm the presence of mouse genomic PCR template in the reaction.

The Ponasterone A inducible expression of both c-myc and abl and the immortalised growth of the cells of interest harvested from the triple transgenic is performed according to protocols described in Example 2 for c-myc and Example 3 for abl.

Example 5

Derivation of Transgenic Mice Expressing Inducible SV40 Large T Antigen Under the Control of the Ecdysone Inducible Expression System This procedure is identical to that described for deriving the c-myc transgenic described in Example 2 except for the following modifications. The coding sequence for the SV40 Large T antigen (GenBank Accession number: AAB59901.1"/db_xref="GI:332753") is PCR amplified from a cDNA library derived from a mouse infected with SV40 virus utilising the following PCR primers, 5'-GTAGCTAGCGCCACCATGGATAGAGT-TCTGAGCAGAG-3' (SEQ ID 7; 5' SV40 Large T primer) and 5'-GATCTCGAGTCAATAAACTGTGTATTCAGC-3' (SEQ ID 8; 3' SV40 Large T primer). The 2,382 bp PCR product is digested with Nhe I and Xho I and the 2,370 bp digested product cloned into the 4,934 bp gel-purified fragment from an Nhe I and Xho I digestion of pIND (Invitrogen; Cat#V705-20) to generate a 7,304 bp plasmid called pIND-Large T. The insert of pIND-Large T is confirmed by sequencing both strands of the cloned PCR product. The insert along with the appropriate expression control elements are cloned into pcDNA2.1 as described in Example 2, except that the PCR product generated with primers SEQ ID 9 and SEQ ID 10 is 3,161 bp, which yields a 3,151 bp product after digestion with Spe I. This digested product is then cloned into pcDNA2.1 to yield a 6,122 bp plasmid called pcDNA2.1-IND-Large T. The homozygous double transgenic mouse line called VgEcR-RXR/IND-Large T is then prepared similarly as that for c-myc described in Example 2 but in this example using the Spe I IND-Large T fragment for mouse injections. Presence of the SD-Large T insert in the blood derived genomic DNA is confirmed using the primers 5'-AACTTG-GCTCCTCCGATGCTC-3' (SEQ ID 15; 5' Large T transgene confirmation primer) and SEQ ID 10 to generate a PCR product of 1,069 bp.

Induction of SV40 Large T antigen expression in the presence of Ponasterone A is demonstrated similarly to c-myc as described in Example 2 except that an anti-SV40 Large T antigen antibody (Santa Cruz; Cat #sc147) is used to detect increased expression of Large T antigen upon induction. The ability to generate immortalised spleen cells with the VgEcR-RXR/IND-Large T mouse line is demonstrated similarly to the method described in Example 2 for the VgEcR-RXR/IND-c-myc line.

Example 6

Derivation of Transgenic Mice Expressing Abl, c-myc and Large T Antigen Under the Control of the Ecdysone Inducible Expression System The VgEcR-RXR/IND-abl/c-myc triple transgenic derived in Example 4 and the VgEcR-RXR/IND-Large T double transgenic derived in Example 5 are crossed to yield a quadrouple homozygous transgenic called VgEcR-RXR/IND-abl/c-myc/Large T. The presence of all four transgenes is confirmed using the following primer pairs to generate PCR products of defined size from genomic DNA harvested from blood samples of the transgenic mice; SEQ ID 16 and 2, 13 and 10, 14 and 10, and 15 and 10 for the confirmation of the presence of VgRXR (1,594 bp), IND-c-myc (309 bp), IND-abl (733 bp) and IND-Large T (1,069 bp) transgenes respectively. The primer pair SEQ ID 11 and 12, which amplifies a 494 bp beta globin gene product is used as a control in each of the above PCR reactions to confirm the presence of mouse genomic PCR template in the sample.

Induction of c-myc, abl and SV40 Large T antigen expression in the presence of Ponasterone A is demonstrated according to protocols described in Example 2 for c-myc, Example 3 for abl and Example 5 for the SV40 Large T antigen. The ability to generate immortalised spleen cells with the VgEcR-RXR/IND-abl/c-myc/Large T mouse line is demonstrated similarly to the method described in Example 2 for the VgEcR-RXR/IND-c-myc line.

Example 7

Derivation of Immortalised Spleen Cell Lines from the Immortomouse

The spleen (other tissues/cell types of interest which may be similarly harvested include tonsil, lymph node, adenoid, appendix, peyer's patches, bronchial-associated lymphoid tissue, bone marrow, mucosa-associated lymphoid tissue or circulating β-lymphocytes) are harvested form an Immortomouse (Jat et al. (1999) U.S. Pat. No. 5,866,759; Jat et al. (1997) U.S. Pat. No. 5,688,692) which has been sacrificed by cervical dislocation. Where required the cells are gently dissociated from the tissue using a 25 g needle and syringe and flushed with RPMI-1640 (Sigma; Cat#R0883). The cells are then split into two aliquots and placed in two separate 50 ml flasks (Greiner; Cat#690175). Both containing 10 ml RPMI-1640 with 2 mM glutamine (Life technologies; Cat#25030-024), 10% Foetal Bovine Serum (Life Technologies; Cat#16000-036) and 100 units Penicillin/100 ug Streptomycin per ml (Life technologies; Cat#15140-114). One flask is incubated at 33° C./5% $CO_2$ while the other maintained at 37° C./5% $CO_2$. Those cells growing at the tsA58 permissive temperature (33° C.) become immortalised and can be further passaged.

Example 8

Derivation of Immortalised Spleen Cell Lines Secreting Antibodies with Desired Specificity from Transgenic Animals Expressing c-myc, abl or c-myc and abl or SV40 Large T Antigen or c-myc, abl and SV40 Large T Antigen Under the Control of the Ecdysone Inducible Expression System as Prepared in Examples 2, 3, 4, 5 and 6, Employing a Standard Mouse Immunisation Schedule Immunization of Mouse with Antigen of Interest The transgenic mouse generated in Example 2, 3, 4, 5 or 6 is immunised with the antigen(s) of interest according to standard protocols familiar to those skilled in the art. The antigen(s) may be any molecule(s) foreign to the mouse but is commonly a protein or small peptide. If a small peptide is to be used as the immunogen this may be chemically coupled to an antigenic carrier protein such as key-hole lympet haemocyanain (KLH), in order to improve the immunogenicity of the peptide. There are many methods of coupling KLH to small peptides. A common route is to engineer a unique cystein residue to either the N- or C-terminus of the peptide and to couple the peptide to KLH via disulphide bridges utilising methods known to those skilled in the art.

By way of example the immunisation protocol may consist of the following steps. First a pre-immunisation tail bleed serum sample is taken from the mouse. On day one the mouse is immunised with the antigen (1-100 micrograms in 0.1-0.5 ml of phosphate-buffered saline) in a 1:1 mixture with Freunds complete adjuvant (Sigma; F5881). The antigen is mixed with an equal volume of Freunds incomplete adjuvant (Sigma; F5506) for the second immunisation performed on day 14. A first test-bleed is taken on day 21 and a further immunisation performed on day 28. Further test bleeds and immunisations are performed on a two-week cycle until a positive antibody response has been determined form the test bleeds (see below).

Test bleeds may be assayed for the presence of the required response by a number of methods familiar to those skilled in the art. By way of example this is achieved using the enzyme-linked immunoabosrbent assay (ELISA). Thus the wells in a microtitre plate are coated with the antigen of interest and blocked. Test bleed serum samples are incubated with the coated wells and then washed. The wells are then incubated with a secondary enzyme linked antibody conjugate. Such a commonly used conjugate is a goat anti-mouse horse-radish peroxidase (HRP) conjugate (Sigma; Cat#A3673). After a further wash of the wells the presence of the HRP conjugate (indicating the presence of mouse antibodies recognising the antigen) may be determined by the addition of a colorimetric substrate such as OPD (Sigma; Cat#P6662). Utilising the above technique, mice may be identified which have successfully developed an immune response to the antigen of interest.

Antigen Labelling

In order to select antibody-secreting cells by fluorescence-activated cell sorting it is necessary to label the antigen of interest with an appropriate fluorophore. The selection is driven by the choice of wavelengths on the cell-sorter available for 'exciting' and reading the 'emission' of the sample to be sorted. By way of example the antigen may be labelled with fluorescein which has a fluorescence excitation maxima of ~494 nm and a fluorescence emission maxima of ~519 nm. Thus cells secreting antibodies with specific binding properties and displaying appropriate cell-surface immunoglobulins are differentially isolated by labelling specific antigens or epitopes of single antigens with different fluorophores each with alternative excitation emission characteristics. The selection of the fluorophores determined by the ability of the detection system of the cell sorter to discriminate between the presence of the different fluorophores in the sample.

Harvesting of the Spleen Cells

The spleen is harvested from the mouse when the ELISA testing of the tail bleeds indicates that a satisfactory response against the antigen of interest has been achieved. In addition, a final immunisation is performed two days prior to sacrifice. The mouse is sacrificed by cervical dislocation and the skin sterilised with ethanol. All further manipulations are performed under sterile conditions. The spleen is removed and a cut is introduced along the length of the organ. Using a 25 g needle 10 ml of RPMI media is used to wash out the cells from the spleen. The 10 ml cell suspension is recovered and the process repeated. The cells are centrifuged at 1000 g for 3 minutes and resuspended in 20 ml of RPMI then centrifuged again at 1000 g for 3 minutes. The cells are then resuspended in 40 ml of DMEM/5 uM Ponasterone A. At this step the spleen cells may be frozen for later use (Bennick et al. 1991; Marusich 1988). The fluorescently labelled antigen(s) is/are added to the cell suspension which is incubated at 37° C. on a gently rotating platform for 1 hour before flow cytometric analysis on a flow cell-sorter such as the Bekton-Dickinson FACSCalibur. The labelled antigen binds to the cell-surface receptor defining β lymphocytes expressing cell-surface immunoglobulins which specifically recognise the fluorescently labelled antigen of interest. Alternatively cells secreting an antibody of interest but not displaying cell-surface antibodies may be selected by the method described by Gray et al. (1995) employing fluorescently labelled and biotinylated antigens. Single cells of interest are plated into single wells of a tissue culture 96 well microtitre plate (containing 0.1 ml of RPMI/10% foetal calf serum/5 uM Ponasterone A per well). The microtitre plates are then incubated at 37° C. and 5% $CO_2$ and the growth of the cells observed over the next few days. The media is replaced with 0.1 ml of fresh RPMI/10% foetal calf serum/5 uM Ponasterone A every 3 days or until the cell colony is approximately 50-70% confluent. At this point 20 ul of the cell supernatant is tested for the presence of antibodies with the required specificity. Such testing may take the form of the ELISA test described above, alternatively more sophisticated assays that closely mimic the final application anticipated for the antibody may be used such as scintillation-proximity, fluorescence or fluorescence polarisation assays. Clones of interest are then sub-cultured from the micro-titre plate into six well plates then into T75 flasks in RPMI/10% FCS/5 uM Ponasterone A. Further sub-culturing either in flasks or at bioreactor scale may then be performed in order to yield sufficient antibody as required. Additionally if required the FACS may be used to identify all β lymphocytes independent of the surface IgG present on the cell. This may be achieved using fluorescently labelled anti-β cell specific mAbs such as anti-B220, CD19, sIgM, sIgD, sIgG, CD23, CD19, CD40, CD79a, CD79b, MHC class II (Hardy et al. 1991; Allman et al. 1993; Erickson et al. 1996). This procedure may be used in combination with the binding of the fluorescently labelled antigen to the β lymphocyte or to a microdroplet harbouring a single cell secreting the antibody of interest, according to the method described by Gray et al. (1995).

Example 9

Employing No Mouse Immunisation Schedule: Derivation of Immortalised Spleen Cell Lines Secreting Antibodies with Desired Specificity from Transgenic Animals Expressing c-myc, abl or c-myc and abl or SV40 Large T Antigen or c-myc, abl and SV40 Large T Antigen under the Control of the Ecdysone Inducible Expression System as Described in Examples 2, 3, 4, 5 and 6.

Spleen cells (or other antibody secreting cells) are harvested (following the method described in Example 8; Harvesting of spleen cells) from a naive mouse (non-immunised) of either the VgEcR-RXR/IND-c-myc (see Example 2), the VgEcR-RXR/IND-abl (see Example 3), the VgEcR-RXR/IND-abl/c-myc (see Example 4), the VgEcR-RXR/IND-Large T (see Example 5) or the called VgEcR-RXR/IND-abl/c-myc/Large T (Example 6) lineage. Immortalised spleen cell lines derived from any of the above lineages secreting the antibody of interest are selected according to the methods described in Example 8 (Antigen labelling and Harvesting of the spleen cells). Alternatively the spleen cells may be frozen after harvest for later use (Bennick et al. 1991; Marusich 1988). Thus a large batch of naïve spleen cells (from several spleens) may be frozen down in several aliquots for later use, thus further simplifying the cell selection methodology as further experiments would require only the thawing out of one vial of cells rather than the sacrifice of a fresh mouse and preparation of the cell sample.

Example 10

Derivation of Immortalised Spleen Cell Lines Secreting Antibodies with Desired Specificity from the Immortomouse as Described in Example 7 Employing a Mouse Immunisation Schedule Immortomice are immunised with the antigen(s) of interest according to the methods described in Example 8 (Immunisation of mouse with antigen of interest). Once an appropriate immune response has been detected the antigen is labelled and the spleen cells harvested according to the methods described in Example 8 (Antigen labelling and Harvesting of the spleen cells). Except that the cell culture is performed in the absence of Ponasterone A and at 33° C.

Example 11

Derivation of Immortalised Spleen Cell Lines Secreting Antibodies with Desired Specificity from the Immortomouse as Described in Example 7 Employing no Mouse Immunisation Schedule Spleen cells are harvested from a naïve mouse (non-immunised) according to the method described in Example 8 (Harvesting of spleen cells) except that the cell culture is performed in the absence of Ponasterone A and at 33° C. Clonal selection of the desired cells is performed employing a cell-sorter according to the protocols described in Example 8 (Antigen labelling and Harvesting of the spleen cells) except that the cell culture is performed in the absence of Ponasterone A and at 33° C. Alternatively the spleen cells may be frozen after harvest for later use (Bennick et al. 1991; Marusich 1988). Thus a large batch of naïve spleen cells (from several spleens) may be frozen down in several aliquots for later use, thus further simplifying the cell selection methodology as further experiments would require only the thawing out of one vial of cells rather than the sacrifice of a fresh mouse and preparation of the cell sample.

Example 12

Derivation of Immortalised Spleen Cell Lines Secreting Antibodies with Desired Specificity Utilising the Methodologies Described in Examples 8, 9, 10 and 11 from Transgenic Animals Expressing c-myc, abl or c-myc and abl or SV40 Large T Antigen or c-myc, abl and SV40 Large T Antigen Under the Control of the Ecdysone Inducible Expression System as Prepared in Examples 2, 3, 4, 5, 6 or the Immortomouse Described in Example 7 after Breeding these Mice to Homozygous with One which is a Null Mutant for the p53 Tumour Suppressor Gene The homozygous p53 null mutant described in Jacks et al. (1994) is bred to double homozygosity with any one of the transgenics described in examples 2 to 7. Cells secreting antibodies with the desired specificity are then derived as described in the appropriate examples 8, 9, 10 or 11.

Example 13

Derivation of Transgenic Mice Providing Humanised Antibodies Utilising the Methodologies Described in Examples 8, 9, 10, 11 and 12 and the Transgenic Mice Described in Examples 2, 3, 4, 5, 6, 7 or 12

Humanised monoclonal antibodies may be generated by crossing one of the transgenic mice described in either Example 2 (VgEcR-RXR/IND-c-myc), Example 3 (VgEcR-RXR/IND-abl), Example 4 (VgEcR-RXR/IND-abl/c-myc), Example 5 VgEcR-RXR/IND-Large T, Example 6 (VgEcR-RXR/IND-abl/c-myc/Large T), Example 7 (Immortomouse) or Example 12 (as 2 to 7 but also p53 −/−) with a mouse in which all or part of the immunoglobulin coding sequence has been replaced with the equivalent human sequences. The two selected mouse lines are bred and PCR analysis of DNA derived from the genomic DNA harvested from the blood of the progeny is screened to ensure that the offspring harbours the required genetic information provided from both transgenic founders. Examples of mice with humanised immunoglobulin sequences that could be used to cross with the mice described in Examples 2, 3, 4, 5, 6 or 7 include the Abgenix Xenomouse TM (Green et al. 1994; Mendez et al. 1997; Kucherlapati et al. (2000) Human antibodies derived from humanised Xenomouse, U.S. Pat. No. 6,150,584; Kucherlapati et al. (2000) Generation of xenogeneic antibodies. U.S. Pat. No. 6,114,598) and the Medarex HuMab-mouse (Lonberg et al. (2001) U.S. Pat. No. 6,300,129). Monoclonal antibodies are then derived utilising the methodologies described in Examples 8 or 9 where immortalisation is achieved by expression of oncogenes under the control of the ecdysone promoter system either with or without a mouse immunisation step respectively or in Examples 10 and 11 for derivation of antibodies from the immortomouse again with or without a mouse immunisation step respectively.

Having described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

REFERENCES

Adams, G. P. and Schier R. (1999) Generating improved single-chain Fv molecules for tumor targetting. *J. Immunol. Methods* 231(1-2), 249-260.

Adams, J. M. and Cory, S. (1985) Myc oncogene activation in B and T lymphoid tumours. *Proc. R. Soc. Lond Biol. Sci.* 226(1242), 59-72.

Adams, J. M., Harris, A. W., Strasser, A., Ogilvy, S. and Cory, S. (1999) Transgenic models of lymphoid neoplasia and development of a pan-hematopoietic vector. *Oncogene* 18(38), 5268-5277.

Albanese, C., Reutens, A. T., Bouzahzah, B., Fu, M., D'Amico, M., Link, T., Nicholson, R., Dephino, R. A. and Pestell, R. G. (2000) Sustained mammary gland-directed, ponasterone A-inducible expression in transgenic mice. *FASEB J.* 14, 877-884.

Allen, K. J., Reyes, R., Demmler, K., Mercer, J. F., Williamson, R. and Whitehead, R. H. (2000) Conditionally immortalized mouse hepatocytes for use in liver gene therapy. *J. Gastroenterol. Hepatol.* 15(11), 1325-1332.

Allman, D. M., Ferguson, S. E., Lentz, V. M. and Cancro, M. P. (1993) Peripheral B cell maturation. II. Heat-stable antigen(hi) splenic B cells are an immature developmental intermediate in the production of long-lived marrow-derived B cells. *J. Immunol.* 151(9), 4431-4444.

Amara, J. F., Clackson, T., Rivera, V. M., Guo, T., Keenan, T., Natesan, S., Pollock, R., Yang, W., Courage, N. L., Holt, D. A. and Gilman, M. (1997) A versatile synthetic dimerizer for the regulation of protein-protein interactions. *Proc. Natl. Acad. Sci. USA* 94, 10618-10623.

Arora, V. and Iversen (2000) Antisense oligonucleotides targeted to the p53 gene modulate liver regeneration in vivo. *Drug Met. Disc.* 28(2), 131-138.

Bennick, A., Gron, B. and Brosstad, F. (1991) Hybridomas can successfully be prepared from frozen/thawn spleen cells. *Hybridoma* 10(6), 761-765.

Boerner, P., Lafond, R., Lu, W. Z., Brams, P. and Royston, I. (1991) Production of antigen-specific human monoclonal antibodies from in vitro-primed human spenocytes. *J. Immunol.* 147(1), 86-95.

Cannell, E. J., Farrell, P. J. and Sinclair, A. J. (1996) Epstein-Barr virus exploits the normal cell pathway to regulate Rb activity during the immortalisation of primary β-cells. *Oncogene* 13(7), 1413-1421.

Carnero, A., Hudson, J. D., Hannon, G. J. and Beach, D. H. (2000) Loss-of-function genetics in mammalian cells: the p53 tumor suppressor model. *Nucleic Acid Res.* 28(11), 2234-2241.

Chambers, T. J., Owens, J. M., Hattersley, G., Jat, P. S. and Noble, M. D. (1993) Generation of osteoclast-inductive and osteoclastogenic cell lines from the H-2KbtsA58 transgenic mouse. *Proc. Natl. Acad. Sci. USA* 90(12), 5578-5582.

Cianfriglia, M., Mariani, M., Armellini, D., Massone, A., Lafata, M., Presentini, R. and Antonio, G. (1986) Methods for high frequency production of soluble antigen-specific hybridomas; specificities and affinities of the monoclonal antibodies obtained. *Methods in Enzymol.* 121, 193-210.

Cianfriglia, M., Nuti, M., Turchi, V., Barca, S., Tombesi, M., Morrone, S., Cenciarelli, C. and Natali, P. G. (1987) High frequency production of hybridomas secreting antibodies to cell antigens. *Hybridoma* 6(6), 673-677.

Citri, Y., Braun, J. and Baltimore, D. (1987) Elevated myc expression and c-myc amplification in spontaneously occurring B lymphoid cell lines. *J. Exp. Med.* 165(4), 1188-1194.

Clackson, T., Yang, W., Rozamus, L. W., Hatada, M., Amara, J. F., Rollins, C. T., Stevenson, L. F., Magari, S. R., Wood, S. A., Courage, N. L., Lu, X., Cerasoli Jr, F., Gilman, M. and Holt, D. (1998) Redesigning an FKBP-ligand interface to generate chemical dimerizers with novel specificity. *Proc. Natl. Acad. Sci. USA* 95, 10437-10442.

Clark, M. R. and Milstein, C. (1981) Expression of spleen cell immunoglobulin phenotype in hybrids with myeloma cell lines. *Somatic Cell Genet.* 7(6), 657-666.

Collins, J. J., Black, P. H., Strosberg, A. D., Haber, E. and Bloch, K. J. (1974) Transformation by Simian Virus 40 of spleen cells from a hyperdirnune rabbit: Evidence for synthesis of immunoglobulin by the transformed cells. *Proc. Natl. Acad. Sci. USA* 71(2), 260-262.

Conrad, M. K. and Lo, M. M. S. (1990) Facilitated cell fusion for hybridoma production. *Methods in Enzymol.* 184, 641-653.

Dangl, J. L. and Herzenberg, L. A. (1982) Selection of hybridomas and hybridoma variants using the fluorescence activated cell sorter. *J. Immunol. Methods* 52(1), 1-14.

De Clercq, L., Cormont, F. and Bazin, H. (1986) Generation of Rat-Rat hybridomas with the use of the LOU IR983F nonsecreting fusion cell line. *Methods in Enzymol.* 121, 2340-238.

Dennis, J. E. and Caplan, A. L. (1996) Analysis of the developmental potential of conditionally immortal marrow-derived mesenchymal progenitor cells isolated from the H-2Kb-tsA58 transgenic mouse. *Connect Tissue Res.* 35(14), 93-99.

Erickson, L. D., Tygrett, L. T., Bhatia, S. K., Grabstein, K. H. and Walderscmidt, T. J. (1996) Differential expression of CD22 (Lyb8) on murine B cells. Differential expression of CD22 (Lyb8) on murine B cells. *Int. Immunol.* 8(7), 1121-1129.

Faller, G., Vollmers, H. P., Weiglein, I., Marx, A., Zink, C., Pfaff, M. and Muller-Hermelink, H. K. (1990) HAB-1, a new heteromyeloma for continuous production of human monoclonal antibodies. *Br. J. Cancer* 62(4), 595-598.

Ferreira, A. and Kosik, K. S. (1996) Accelerated neuronal differentiation induced by p53 suppression. *J. Cell Sci.* 109, 1509-1516.

Flynn, J. N., Harkiss, G. D. and Hopkins, J. (1989) Generation of a sheep×mouse heterohybridoma cell line (1C6.3a6T.1D7) and evaluation of its use in the production of ovine monoclonal antibodies. *J. Immunol. Methods* 121 (2), 237-246.

Foung, S. K. and Perkins, S. (1989) Electric field-induced cell fusion and human monoclonal antibodies. *J. Immunol. Methods* 116(1), 117-122.

Foung, S., Perkins, S., Kafadar, K., Gessner, P. and Zimmermann, U. (1990) Development of microfusion techniques to generate human hybridomas. *J. Immunol. Methods* 134 (1), 35-42.

Fuchs, S. Y., Adler, V., Wu, X. Ronai, Z. (1998) Mdm2 association with p53 targets its ubiquitination. *Oncogene* 17(19), 2543-2547.

Gauwerky, C. E., Haluska, F. G., Tsujimoto, Y., Nowell, P. C. and Croce, C. M. (1988) Evolution of B-cell malignancy: Pre-B-cell leukemia resulting from MYC activation in a B-cell neoplasm with a rearranged BCL2 gene. *Proc. Natl. Acad. Sci. USA* 85(22), 8548-8552.

Gray, F., Kenney, J. S. and Dunne, J. F. (1995) Secretion capture and report web: use of affinity derivatized agarose microdroplets for the selection of hybridoma cells. *J. Immunol. Methods* 182, 155-163.

Green, L. L., Hardy, M. C., Maynard-Currie, C. E., Tsuda, H., Louie, D. M., Mendez, M. J., Abderrahim, H., Noguchi, M., Smith, D. H. and Zeng, Y et al. (1994) Antigen-specific human monoclonal antibodies from mice engineered with human Ig heavy and light chain YACs. *Nat. Genet.* 7(1), 13-21.

Grunow, J. S., Kiessig, S. T., Settmacher, U. and Von Baehr, R. (1990) Strategies in the development of human monoclonal antibodies. *Dev. Biol. Stand.* 71, 3-7.

Guidry, A. J., Srikumaran, S. and Goldsby, R. A. (1986) Production and characterisation of bovine immunglobulins from bovine×murine hybridomas. *Methods in Enzymol.* 121, 244-265.

Gustafsson, B., Jondal, M. and Sunqvist, V. A. (1991) SPAM-8, a mouse-human heteromyeloma fusion partner in the production of human monoclonal antibodies. Establishment of a human monoclonal antibody against cytomegalovirus. *Hum. Antibodies Hybridomas* 2(1), 26-32.

Hardy, R. R., Carmack, C. E., Shinton, S. A., Kemp, J. D. and Hayakawa, K. (1991) Resolution and characterization of Pro-B and Pre-Pro-B cell stages in normal mouse bone marrow. *J. Exp. Med.* 173(5), 1213-1225.

Hariharan, I. K., Harris, A. W., Crawford, M., Abud, H., Webb, E., Cory, S. and Adams, J. M. (1989) A bcr-v-abl oncogene induces lymphomas in transgenic mice. *Mol. Cell Biol.* 9(7), 2798-2805.

Harris, A. W., Bath, M. L., Rosenbaum, H., McNeall, J., Adams, J. M. and Cory, S. (1990) Lymphoid tumorigenesis by v-abl and BCR-v-abl in transgenic mice. *Curr. Top. Microbiol. Immunol.* 166, 165-173.

Haupt, Y., Maya, R., Kazaz, A. and Oren, M. (1997) Mdm2 promotes the rapid degradation of p53. *Nature* 387, 296-299.

Hennigan, R. F. and Stambrook, P. J. (2001) Dominant negative c-jun inhibits activation of the cyclin D1 and cyclin E kinase complexes. *Mol. Biol. Cell.* 12, 2352-2363.

Hewish, D. R. and Werkineister, J. A. (1989) The use of an electroporation apparatus for the production of murine hybridomas. *J. Immunol. Methods* 120(2), 285-289.

Ho, S. N., Biggar, S. R., Spencer, D. M., Schreiber, S. L. and Cabtree, G. R. (1996) Dimeric ligands define a role for transcriptional activation domains in reinitiation. *Nature* 382(6594), 822-826.

Hollyoake, M., Stuhler, A., Farrell, P., Gordon, J. and Sinclair, A. (1995) The normal cell cycle activation program is exploited during the infection of quiescent B lymphocytes by Epstein-Barr virus. *Cancer Res.* 55(21), 4784-4787.

Hui, S. W. and Stenger, D. A. (1993) Electrofusion of cells: Hybridoma production by electrofusion and polyethylene glycol. *Methods in Enzymol.* 220, 212-227.

Igarashi, M. and Bando, Y. (1990) Enhanced efficiency of cell hybridization by neuramidase treatment. *J. Immunol. Methods* 135(1-2), 91-93.

Jacks, T., Remington, L., Williams, B. O., Schmitt, E. M., Halachmi, S., Bronson, R. T. and Weinberg, R. A. (1994) Tumor spectrum analysis in p53-mutant mice. *Curr. Biol.* 4(1), 1-7.

Jantscheff, P., Winkler, L., Karawajew, L., Kaiser, G., Bottger, V. and Micheel, B. (1993) Hybrid hybridomas producing bispecific antibodies to CEA and peroxidase isolated by a combination of HAT medium selection and fluorescence activated cell sorting. *J. Immunol Methods* 163(1), 91-97.

Jagger, D. J., Holley, M. C. and Ashmore, J. F. (1999) Ionic currents expressed in a cell line derived from the organ of Corti of the Immortomouse. *Pflugers Arch—Eur J Physiol.* 438, 8-14.

Jagger, D. J., Griesinger, C. B., Rivolta, M. N., Holley, M. C. and Ashmore, J. F. (2000) Calcium signalling mediated by the alpha-9 acetylcholine receptor in a cochlear cell line from the Inmmortomouse. *J. Physiol.* 527.1, 49-54.

Jat, P. S., Noble, M. D., Ataliotis, Y., Tanaka, N., Yannoutsos, L., Larsen L. and Kioussis, D. (1991) Direct derivation of conditionally immortal cell lines from an $H-2K^b$-tsA58 transgenic mouse. *Proc. Natl. Acad. Sci. USA* 88, 5096-5100.

Jat, P. S. and Sharp, P. A. (1989) Cell lines established by a temperature-sensitive Simian virus 40 large-T-antigen gene are growth restricted at the nonpermissive temperature. *Mol. Cell Biol.* 9(4), 1672-1681.

Kanda, S., Lerner, E. C., Tsuda, S., Shono, T., Kanetake, H. and Smithgall, T. E. (2000) The nonreceptor protein-tyrosine kinase c-Fes is involved in fibroblast growth factor-2-induced chemotaxis of murine brain capillary endothelial cells. *J. Biol. Chem.* 275(14), 10105-10111.

Kanid, T. and Takeuchi, S. (1995) Immortalization of plasma cells by plasmid DNA and its hybridoma. *Hum. Antibodies Hybridomas* 6(3), 89-92.

Karns, L. R., Kisielewski, A., Gulding, K. M., Seraj, J. M. and Theodorescu, D. (2001) Measurement of gene expression by an ecdysone-inducible gene switch in tumor xenografts. *BMC Biotechnology* 1, 11-22.

Karsten, U., Stolley, P. and Seidel, B. (1993) Polyethylene glycol and electric field-mediated cell fusion for formation of hybridomas. *Methods in Enzymol.* 220, 228-238.

Katakura, Y., Alam, S. and Shirahata, S. (1998) Immortalization by gene transfection. *Methods Cell Biol.* 57, 69-91.

Kawahara, H., Shirahata, S., Tachibana, H. and Murakami, H. (1992) In vitro immnunization of human lymphocytes with human lung cancer cell line A549. *Hum. Antibodies Hybridomas* 3(1), 8-13.

Kawahara, H., Yamada, K., Shirahata, S. and Murakami, H. (1990) A new human fusion partner, HK-128, for making human-human hybridomas producing monoclonal IgG antibodies. *Cytotechnology* 4(2), 139-143.

Kenney, J. S., Gray, F., Ancel, M. H. and Dunne, J. F. (1995) Production of monoclonal antibodies using a secretion capture report web. *Biotechnology (NY)* 13(8), 787-790.

Klein, G. (1981) The role of gene dosage and genetic transpositions in carcinogenesis. *Nature* 294, 313-318.

Klein, G. (1988) Immunological aspects of B-cell derived tumors in humans and rodents. *Princess Takamatsu Symp.* 19, 3-13.

Kohler, G. and Milstein, C. (1975) Continuous cultures of fused cells secreting antibody of predefined specificity. *Nature* 256, 495-497.

Kohler, G., Pearson, T. and Milstein, C. (1977) Fusion of T and B cells. *Somatic cell Genet.* 3(3), 303-312.

Kollias, G., Wrighton, N., Hurst, J. and Grosveld, F. (1986) Regulated expression of human A gamma-, beta-, and hybrid gamma beta-globin genes in transgenic mice: manipulation of the developmental expression patterns. *Cell* 46(1), 89-94.

Kovalchuk, A. L., Qi, C. F., Torrey, T. A., Taddesse-Heath, L., Feigenbaum, L., Park, S. S., Gerbitz, A., Klobeck, G., Hoertnagel, K., Polack, A., Bornkamm, G. W., Janz, S. and Morse, H. C. $3^{rd}$ (2000) Burkitt lymphoma in the mouse. *J. Exp. Med.* 192(8), 1183-1190.

Kubbutat, M. H., Jones, S. N. and Vousden, K. H. (1997) Regulation of p53 stability by Mdm2. *Nature* 387, 299-303.

Kumar, A., Ta, D., Henderson, D., Mushinski, J. F., Reed, J. C., Kuus-Reichel, K. and Saedi, M. S. (1999) bcl2 and v-abl oncogenes cooperate to immortalize murine B cells that secrete antigen specific antibodies. *Immunol. Lett.* 65(3), 153-159.

Lane, R. D. (1985) A short-duration polyethylene glycol fusion technique for increasing production of monoclonal antibody-secreting hybridomas. *J. Immunol. Methods* 81(2), 223-228.

Lane, R. D., Crissman, R. S. and Ginn, S. (1986) High efficiency fusion procedure for producing monoclonal antibodies against weak immunogens. *Methods in Enzymol.* 121, 183-192.

Lane, R. D., Crissman, R. S. and Lachman, M. F. (1984) Comparison of polyethylene glycols as fusogens for producing lymphocyte-myeloma hybrids. *J. Immunol. Methods* 72(1), 71-76.

Langdon, W. Y., Harris, A. W., Cory, S. and Adams, J. M. (1986) The c-myc oncogene perturbs B lymphocyte development in E-mu-myc transgenic mice. *Cell* 47(1), 11-18.

Lee, G. H., Ogawa, K. and Drinkwater, N. R. (1995) Conditional transformation of mouse liver epithelial cells. An in vitro model for analysis of genetic events in hepatocarcinogenesis. *Am. J. Pathol.* 147(6), 1811-1822.

Liu, B. Y., Guo, J., Lanske, B., Divieti, P., Kronenberg, H. M. and Bringhurst, F. R. (1998) Conditionally immortalized murine bone marrow stromal cells mediate parathyroid hormone-dependent osteoclastogenesis in vitro. *Endocrinology* 139(4), 1952-1964.

Lo, M. M., Tsong, T. Y., Conrad, M. K., Strittmatter, S. M., Hester, L. D. and Snyder, S. H. (1984) Monoclonal antibody production by receptor-mediated electrically induced cell fusion. *Nature* 310(5980), 792-794.

Lumanglas, A. L. and Wang, B. S. (1995) Production of monoclonal antibodies in swine. *Methods Mol. Biol.* 45, 49-54.

Maki, C. G. and Howley, P. M. (1997) Ubiquitination of p53 and p21 is differentially affected by ionizing and UV radiation. *Mol. Cell. Biol.* 17(1), 355-363.

Malynn, B. A., de Alboran, I. M., O'Hagan, R. C., Bronson, R., Davidson, L., DePinho, R. A. and Alt, F. W. (2000) N-myc can functionally replace c-myc in murine development, cellular growth and differentiation. *Genes Dev.* 14(11), 1390-1399.

Manickan, E., Satoi, J., Wang, T. C. and Liang, T. J. (2001) Conditional liver-specific expression of simian virus 40 T antigen leads to regulatable development of hepatic neoplasm in transgenic mice. *J. Biol. Chem.* 276(17), 13989-13994.

Martel, F. and Bazin, R., Verrette, S. and Lemieux, R. (1988) Characterization of higher avidity monoclonal antibodies produced by murine B-cell hybridoma variants selected for increased antigen binding of membrane Ig. *J. Immunol. Methods* 141(5), 1624-1629.

Marusich, M. F. (1988) Efficient hybridoma production using previously frozen splenocytes. *J. Immunol. Methods* 114 (1-2), 155-159.

Matsumoto, H. N., Tamura, M., Denhlardt, D. T., Obinata, M. and Noda, M. (1995) Establishment and characterization of bone marrow stromal lines that support osteoclastogenesis. *Endocrinology* 136(9), 4048-4091.

Matsushita, H., Morishita, R., Aoki, M., Tomita, N., Taniyama, Y., Nakagami, H., Shimozato, T., Higaki, J., Kaneda, Y and Ogihara, T. (2000) Transfection of antisense p53 tumor suppressor gene oligodeoxynucleotides into rat carotid artery results in abnormal growth of vascular smooth muscle cells. *Circulation* 101, 1447-1452.

Mendez, M. J., Green, L. L., Corvalan, J. R., Jia, X. C., Maynard-Currie, C. E., Yang, X. D., Gallo, M. L., Louie, D. M., Lee, D. V., Erickson, K. L., Luna, J., Roy, C. M., Abderrahim, H., Kirschenbaurn, F., Noguchi, M., Smith, D. H., Fukushima, A., Hales, J. F., Klapholz, S., Finer, M. H., Davis, C. G., Zsebo, K. M. and Jakobovits, A. (1997) Functional transplant of megabase human immunoglobulin loci recapitulates human antibody response in mice. *Nature Genetics* 15(2), 146-156.

Moore, L. R., Zborowski, M., Sun., L. and Chalmers, J. J. (1998) Lymphocyte fractionation using immunomagnetic colloid and a dipole magnet flow cell sorter. *J. Biochem. Biophys. Methods* 37(1-2), 11-33.

Mostecki, J., Halgren, A., Radfar, A., Sachs, Z., Ravitz, J., Thome, K. C. and Rosenberg, N. (2000) Loss of heterozygosity at the Ink-4a/Arf locus facilitates abelson virus transformation of pre-B cells. *J. Virol.* 74(20), 9479-9487.

Niedbla, W. G. and Stott, D. I. (1998) A comparison of three methods for production of human secreting autoantibodies. *Hybridoma* 17(3), 299-304.

No, D., Yao, T-P. and Evans, R. M. (1996) Ecdysone-inducible gene expression in mammalian cells and transgenic mice. *Proc. Natl. Acad. Sci. USA* 93, 3346-3351.

Noble, M., Groves, A. K., Ataliotis, P., Ikram, Z. and Jat, P. S. (1995) The H-2KbtsA58 transgenic mouse: A new tool for the rapid generation of novel cell lines. *Transgenic Res.* 4(4), 215-225.

O'Hare, M. J., Bond, J., Clarke, C., Takeuchi, Y., Atherton, A. J., Berry, C., Moody, J., Silver, A. R. J., Davies., D. C., Alsop, A. E., Munro Neville, A. and Jat, P. S. (2001) Conditional immortalization of freshly isolated human mammary fibroblasts and endothelial cells. *Proc. Natl. Acad. Sci. USA* 98(2), 646-651.

Ostberg, L. (1986) Human×(Mouse×Human) hybridomas. *Methods in Enzymol.* 121, 228-234.

Overell, R. W., Weisser, K. E., Hess, B., Namen, A. E. and Grabstein, K. H. (1989) Stage-specific transformation of murine B lineage cells by ras and myc. *Oncogene* 4(12), 1425-1432.

Palomo, C., Zou, X., Nicholson, I. C., Butzler, C. and Muggemann, M. (1999) B-Cell tumorigenesis in mice carrying a yeast artificial chromosome-based Immunoglobulin Heavy/c-myc translocus is independent of the heavy chain enhancer (Eμ). *Cancer Research* 59, 5625-5628.

Panova, I. and Gustafsson, B. (1995) Increased human hybridoma formation by electrofusion of hurman B cells with heteromyeloma SPAM-8 cells. *Hybridoma* 14(3), 265-269.

Parks, D. R., Bryan, V. M., Oi, V. T. and Herzenberg, L. A. (1979) Antigen-specific identification and cloning of hybridomas with a fluorescence-activated cell sorter. *Proc. Natl. Acad. Sci (USA)* 76(4), 1962-1966.

Pasqualucci, L., Neumeister, P., Goossens, T., Nanjangud, G., Chaganti, R. S., Kuppers, R. and Dalla-Pavera, R. (2001) Hyperrutation of mutiple proto-oncogenes in B-cell diffuse large-cell lyrmphomas. *Nature* 412(6844), 341-346.

Pelicci, P. G., Knowles, D. M. 2$^{nd}$, Arlin, Z. A., Wieczorek, R., Luciw, P., Dina, D., Basilico, C. and Dalla-Favera, R. (1986) Multiple monoclonal B cell expansions and c-myc oncogene rearrangements in acquired immune deficiency syndrome-related lymphoproliferative disorders. Implications for lymphomagenesis. *J. Exp. Med.* 164(6), 2049-2060.

Pipas, J. M and Levine, A. J. (2001) Role of T antigen interactions with p53 in turnorigenesis. *Semin. Cancer Biol.* 11(1), 23-30.

Pollock, R. and Rivera, V. M. (1999) Regulation of gene expression with synthetic dimerizers. *Methods in Enzymol.* 306, 263-281.

Pomerantz, J. L., Sharp, P. A. and Pabo, C. O. (1995) Structure-based design of transcription factors. *Science* 267(5194), 93-96.

Pravtcheva, D. D. and Ruddle, F. H. (1983) Normal X chromosome induced reversion in the direction of chromosomes segregation in mouse-Chinese hamster somatic cell hybrids. *Exp. Cell Res.* 148(1), 265-272.

Radna, R. L., Caton, Y., Jha, K. K., Kaplan, P., Li, G., Traganos, F. and Ozer, H. L. (1989) Growth of immortal simian virus 40 tsA-transformed human fibroblasts is temperature dependent. *Mol. Cell Biol.* 9(7), 3093-3096.

Raymon, H. K., Thode, S., Zhou, J., Friedman, G. C., Pardinas, J. R., Barrere, C., Johnson, R. M. and Sah, D. W. Y. (1999) Immortalized human dorsal root ganglion cells differentiate into neurons with nociceptive properties *J. Neurosci.* 19(13), 5420-5428.

Reason, D., Carminati, J., Kimura, J. and Henry, C. (1987) Directed fusion in hybridoma production. *J. Immunol. Methods* 99(2), 253-257.

Rivera, V. M., Clackson, T., Natesan, S., Pollock, R., Amara, J. F., Keenan, T., Magari, S. R., Philips, T., Courage, N. L., Cerasoli Jr, F., Holt, D. A. and Gilma, M. (1996) A humanized system for pharrnacologic control of gene expression. *Nature (medicine)* 2(9), 1028-1032.

Rosenbaum, H., Harris, A. W., Bath, M. L., McNeall, J., Webb, E., Adams, J. M. and Cory, S. (1990) An $E_\mu$-v-abl transgene elicits plasmacytomas in concert with an activated myc gene. *EMBO J.* 9(3), 897-905.

Rosenbaum, H., Webb, Adams, J. M., Cory, S. and Harris, A. W. (1989) N-myc transgene promotes B lymphoid proliferation, elicits lymphomas and reveals cross-regulation with c-myc. *EMBO J.* 8(3), 749-755.

Rush, J. S. and Hodgkin, P. D. (2001) B cells activated via CD40 and IL-4 undergo a division burst but require continued stimulation to maintain division, survival and differentiation. *Eur. J. Immunol.* 31(4), 1150-1159

Ryding, A. D. S., Sharp, M. G. F. and Mullins, J. J. (2001) Conditional transgenic technologies. *J. Endocrin.* 171, 1-14.

Sadigh, S., Scott, B. B., Mageed, R. A., Malcolm, A., Andrew, E. M. and Maini, R. N. (1994) Identification of hybridomas derived from mouse CD5+B lymphocytes by fluorescent staining for cytoplasmic CD5 expression. *Immunology* 81(4), 558-563.

Saez, E., Nelson, M. C., Eshelman, B., Banayo, E., Koder, A., Cho, G. J. and Evans, R. M. (2000) Identification of ligands and coligands for the ecdysone-regualted gene switch. *Proc. Natl. Acad. Sci. USA* 97(26), 14512-14517.

Sanchez-Madrid, F. and Springer, T. A. (1986) Production of Syrian and Arnenian hamster monoclonal antibodies of defined specificity. *Methods in Enzymol.* 121, 239-244.

Schmitt, J. J, Zimmermann, U. and Neil, G. A. (1989) Efficient generation of stable antibody forming hybridoma cells by electrofusion. *Hybridoma* 8(1), 107-115.

Schreiber, S. L. (1991) Chemistry and biology of the immunophilins and their immunosuppressive ligands. *Science* 251(4991), 283-287.

Sethupathi, P., Spieker-Polet, H., Polet, H., Yam, P. C., Tunyaplin, C. and Knight, K. L. (1994) Lymphoid and non-lymphoid tumors in $E_\kappa$-myc transgenics. *Leukemia* 8(12), 2144-2155.

Sharpless, N. E., Bardeesy, N., Kee-Ho, L., Carrasco, D., Castrillon, D. H., Aguirre, A. J., Wu, E. A., Horner, J. W. and DePinho, R. A. (2001) Loss of $p16^{Ink4a}$ with retention of $p19^{Arf}$ predisposes mice to tumorigenesis. *Nature* 413, 86-91.

Shih, A., Davis, F. B., Lin, H. Y. and Davis, P. J. (2002) Resvatrol induces apoptosis in thyroid cancer cell lines via a MAPK- and p53-dependent mechanism. *J. Clin. Endocrinol. Metab.* 87(3), 1223-1232.

Siraganian, R. P., Fox, P. C. and Berenstein, E. H. (1983) Methods of enhancing the frequency of antigen-specific hybridomas. *Methods in Enzymol.* 92, 17-26.

Spencer, D. M. (1996) Creating conditional mutations in mammals. *Trends Genet.* 12(5), 181-187.

Spieker-Polet, H., Sethupathi, P., Yam, P-C. and Knight, K. L. (1995) Rabbit monoclonal antibodies: Generating a fusion partner to produce rabbit-rabbit hybridomas. *Proc. Natl. Acad. Sci. USA* 92, 9348-9352.

Stahl, C., Staehelin, T. and Miggiano, V. (1983) Spleen cell analysis and optimal immunization for high-frequency production of specific hybridomas. *Methods in Enzymol.* 92, 26-36.

Stanton, L. W., Watt, R. and Marcu, K. B. (1983) Translaocation, breakage and truncated transcripts of c-myc oncogene in murine plasmacytomas. *Nature* 303, 401-406.

Steenbakkers, P. G. A., van Meel, F. C. M. and Olijve, W. (1992) A new approach to the generation of human or murine antibody producing hybridomas. *J. Immunol. Methods* 152, 69-77.

Strosberg, A. D., Collins, J. J., Black, P. H., Malarnud, D., Wilbert, S., Bloch, K. J. and Haber, E. (1974) Transformation by simian virus 40 of spleen cells from a hyperimnune rabbit: Demonstration of production of specific antibody to the immunizing antigen. *Proc Natl. Acad. Sci. USA* 71(2), 263-264.

Sugiyama, H., Wang, Y., Jackson, P., Sawyers, C. L. and Klein, G (1994) Molecular requirements for rapid plasmacytoma and pre-B lymphoma induction by Abelson murine leukamia virus in myc-transgenic mice. *Int. J. Cancer* 58(1), 135-141.

Symonds, H. S., McCarthy, S. A., Chen, J., pipas, J. M. and Van. Dyke, T. (1993) Use of transgenic mice reveals cell-specific trasnformation by a simian virus 40 T-antigen amino-terminal mutant. *Mol. Cell. Biol.* 13(6), 3255-32565.

Taggart, R. T. and Samloff, I. M. (1982) Stable antibody-producing hybridomas. *Science* 219, 1228-1230.

Takacs-Jarrett, M., Sweeney, W. E., Avner, E. D. and Cotton, C. U. (1998) Morphological and functional characterisation of a conditionally immortalised collecting tubule cell line. *Am. J. Physiol.* 275 (*Renal Physiol.* 44), F802-F811.

Tavelin, S., Milovic, V., Ocklind, G., Olsson, S. and Artursson, P. (1999) A conditionally immortalized epithelial cell line for studies of intestinal drug transport. *J. Pharmacol. Exp. Therapeu.* 290(3), 1212-1221.

Tomita, M. and Tsong, T. Y. (1990) Selective production of hybridoma cells: Antigenic-based pre-selection of B lymphocytes for electrofusion with myeloma cells. *Biochim. Biophys. Acta.* 1055(3), 199-206.

Tornell, J., Farzad, S., Espander-Jansson, A., Matejka, G., Isaksson, O. and Rymo, L. (1996) expression of Epstein-Barr nuclear antigen 2 in the kidney tubule cells induce tumors intransgenic mice. *Oncogene* 12(7), 1521-1528.

Tsong, T. Y. and Tomita, M. (1993) Selective B lymphocyte-myeloma cell fusion. *Methods in Enzymol.* 220, 238-246.

Tsuchiyama, L., Kieran, J., Boyle, P. and Wetzel, G. D. (1997) Synergy between anti-CD40 mAb and Epstein-Barr virus in activation and transformation of human B lymphocytes. *Hum. Antibodies* 8(1), 43-47.

van Duijn, G., Langedijk, J. P., de Boer, M. and Tager, J. M. (1989) High yields of specific hybridomas obtained by electrofusion of murine lymphocytes immunized in vivo or in vitro. *Exp. Cell Res.* 183(2), 463-472.

Van Mourik, P., Rivero, R. A., van der Kwast, T. H., Lansdorp, P. M. and Zeijlemaker, W. P. (1984) Density separation of spleen cells increases fusion frequency and yield of Ig-producing hybridomas. *J Immunol. Methods* 68, 45-53.

Van Mourik, P. and Zeijlemaker, W. P. (1986) Improved hybridoma technology: Spleen cell separation and soluble growth factors. *Methods in Enzymol.* 121, 174-182.

Virley, D., Ridley, R. M., Sinden, J. D., Kershaw, T. R., Harland, S., Rashid, T., French, S., Sowinski, P., Gray, J. A., Lantos, P. L. and Hodges, H. (1999) Primary CA1 and conditionally immortal MHP36 cell grafts restore conditional discrimination learning and recall in marmosets after excitotoxic lesions of the hippocampal CA1 field. *Brain* 122, 2321-2335.

Walper, J. S., Grunow, R., Heym, S., Volk, H. D. and von Baehr, R. (1990) The hybridization of EBV-immortalized human B-lymphocytes with a human-mouse heteromyeloma cell line. *Allerg. Immunol. (Leipz)* 36(4), 359-365.

Walter, G., Konthur, Z. and Lehrach, H. (2001) High-throughput screening of surface displayed gene products. *Comb. Chem. Throughput Screen* 4(2), 193-205.

Wang, Y., DeMayo, F. J., Tsai, S. Y., O'Malley, B. W. (1997a) Ligand-inducible and liver-specific target gene expression in transgenic mice. *Nature Biotechnol.* 15(3), 239-243.

Wang, Y., O'Malley, B. W. and Tsai, S. Y. (1997b) Inducible system designed for future gene therapy. *Methods Mol. Biol.* 63, 401-413.

Wang, Y., Tsai, S. Y. and O'Malley, B. W. (1999) Antiprogestin regulable gene switch for induction of gene expression in vivo. *Methods in Enzymol.* 306, 281-294.

Weiss, E. H., Mellor, A., Golden, L., Fahrner, K., Simpson, E., Hurst, J. and Flavell, R. A. (1983) The structure of a mutant H-2 gene suggests that the generation of polymorphism in H-2 genes may occur by gene conversion-like events. *Nature* 301(5902), 671-674.

Werkmeister, J. A., Tebb, T. A., Kirlkpatrick, A. and Shukla, D. D. (1991) The use of peptide-mediated elcetrofusion to select monoclonal antibodies directed against specific and homologous regions of the potyvirus coat protein *J. Immunol. Methods* 143(2), 151-157.

Westerwoudt, R. J. (1985) Improved fusion methods. IV. Technical aspects. *J. Immunol. Methods* 77(2), 181-196.

Westerwoudt, R. J. (1986) Factors affecting production of monoclonal antibodies. *Methods inEnzymol* 121, 3-18.

Whitehead, R. H., VanEeden, P. E., Noble, M. D., Ataliotis, P. and Jat, P. S. (1993) Establishment of conditionally immortalized epithelial cell lines from both colon and small intestine of adult H-2K$^b$-tsA58 transgenic mice. *Proc. Natl. Acad. Sci. USA* 90, 587-591.

Windle, J. J., Weiner, R. I. and Mellon, P. L. (1990) Cell lines of the pituitary gonadotrope lineage derived by targeted oncogenesis in transgenic mice. *Mol. Endocrinol.* 4(4), 597-603.

Wolter, S., Mushinski, J. F., Saboori, A. M., Resch, K. and Kracht, M. (2001) Inducible expression of a constitutively active mutant of MAP kinase kinase (MKK) 7 specifically activates JUN N-terminal protein kinase (JNK), alters expression of at least nine genes, and inhibits cell proliferation. *J. Biol. Chem.* 277(5), 3576-3584.

Xirodimas, D., Saville, M. K., Edling, C., Lane, D. P. and Lain, S. (2001) Different effects of p14ARF on the levels of ubiquitinated p53 and mdm2 in vivo. *Oncogene* 20, 4972-4983.

Yu, D. and Thomas-Tikhonenko, A. (2002) A non-transgenic mouse model for B-cell lymphoma: in vivo infection of p53-null bone marrow progenitors by a Myc retrovirus is sufficient for tumorigenesis. *Oncogene* 21, 1922-1927.

Yuan, C., Chen, A., Kolb, P. and Moy, V. T. (2000) Energy landscape of streptavidin-biotin complexes measured by atomic force microscopy. *Biochemistry* 39(33), 10219-10223.

Zhang, G., Slaughter, C. and Humphries, E. H. (1995) v-rel induces ectopic expression of an adhesion molecule, DM-GRASP, during B-lymphoma development. *Mol. Cell Biol.* 15(3), 1806-1816.

Zhu, Y., Mao, X. O., Sun, Y., Xia, Z. and Greenberg, D. A. (2002) p38 Mitogen-activated protein kinase mediates hypoxic regulation of mdm2 and p53 in neurons. J. Biol. Chem. In press.

Sequences

SEQ ID 1
5' VgEcR-RXR primer
5'-GTACTAGTAGGGATTTTGGTCATGGCTAG-3'

SEQ ID 2
3' VgEcR-RXR primer
5'-GTACTAGTCAGCTGGTTCTTTCCGCCTCAG-3'

SEQ ID 3
5' c-myc primer
5'-GTAGCTAGCGCCACCATGCCCGTCAACGTGAACTTC-3'

SEQ ID 4
3' c-myc primer
5'-GATCTCGAGTTATGCACCAGAGTTTCGAAG-3'

SEQ ID 5
5' abl primer
5'-GTAGCTAGCGCCACCATGGAGCCTGGTGGAGTTGGC-3'

SEQ ID 6
3' abl primer
5'-GATCTCGAGTCAAGCTTGCTGTCCAAGATC-3'

SEQ ID 7
5' SV40 Large T primer
5'-GTAGCTAGCGCCACCATGGATAGAGTTCTGAGCAGAG-3'

SEQ ID 8
3' SV40 Large T primer
5'-GATCTCGAGTCAATAAACTGTGTATTCAGC-3'

SEQ ID 9
5' pIND vector primer
5'-GTACTAGTTGCCACCTGACGTCGACGGATC-3'

SEQ ID 10
3' pIND vector primer
5'-GTACTAGTCTCAGAAGCCATAGAGCCCAC-3'

SEQ ID 11
5' beta globin primer
5'-CCAATCTGCTGACAGAGGATAGAGAGGGCAGG-3'

SEQ ID 12
3' beta globin primer
5'-CCTTGAGGCTGTCCAAGTGATTCAGGCCATCG-3'

SEQ ID 13
5' c-myc transgene confirmation primer
5'-ACAGCTTCGAAACTCTGGTGC-3'

SEQ ID 14
5' abl transgene confirmation primer
5'-AGCTGCCCTGCACCTTTCCTG-3'

SEQ ID 15
5' Large T transgene confirmation primer
5'-AACTTGGCTCCTCCGATGCTC-3'

SEQ ID 16
5' VgEcR-RXR transgene confirmation primer
5'-CAGCTGCATTCTCCCATCAGC-3'

The invention claimed is:

1. A method for producing immortalised antibody-secreting cells, comprising:
   (a) providing a germline transgenic mouse having antibody-secreting cells capable of expressing one or more transgenes, wherein the antibody-secreting cells are in a non-immortalised state in the absence of a stimulus and change to an immortalised state by means of the transgene or transgenes upon exposure of the cells to the stimulus;
   (b) extracting the antibody-secreting cells from the mouse; and
   (c) exposing the antibody-secreting cells to the stimulus, thereby immortalising the antibody-secreting cells by means of the transgene or transgenes.

2. A method for producing antibodies, comprising producing immortalised antibody-secreting cells by a method as defined in claim 1, and collecting antibodies from the cells.

3. A method for preparing a clonal population of immortalised cells which produce a monoclonal antibody, comprising:
   (a) providing a germline transgenic mouse having antibody-secreting cells capable of expressing one or more transgenes, wherein the antibody-secreting cells are in a non-immortalised state in the absence of a stimulus and change to an immortalised state by means of the transgene or transgenes upon exposure of the cells to the stimulus;
   (b) extracting the antibody-secreting cells from the mouse;
   (c) exposing the antibody-secreting cells to the stimulus, thereby immortalising the antibody-secreting cells by means of the transgene or transgenes;
   (d) selecting an immortalised antibody-secreting cell which produces the antibody, and
   (e) preparing the clonal population of immortalised cells from the immortalised antibody-secreting cell.

4. A method according to claim 1, wherein expression of a transgene in the antibody-secreting cells is under the control of an inducible promoter, and the stimulus is capable of regulating activity of the promoter and transgene expression.

5. A method according to claim 4, wherein the stimulus promotes promoter activity and transgene expression.

6. A method according to claim 4, wherein the stimulus inhibits promoter activity and transgene expression.

7. A method according to claim 1, wherein a product of a transgene in the antibody-secreting cells promotes immortalisation in the presence of the stimulus, and does not promote immortalisation in the absence of the stimulus.

8. A method according to claim 1, wherein the transgene is an oncogene.

9. A method according to claim 8, wherein the oncogene is a gene for the large T antigen.

10. A method according to claim 1, wherein the transgenic mouse is an immortomouse.

11. A method according to claim 1, wherein a product of a transgene in the antibody-secreting cells inhibits immortalisation in the absence of the stimulus, and does not inhibit immortalisation in the presence of the stimulus.

12. A method according to claim 11, wherein the transgene is a tumour suppressor gene.

13. A method according to claim 1, wherein a product of a transgene in the antibody-secreting cells inhibits a tumour suppressor function in the cells.

14. A method according to claim 13, wherein the transgene is mdm2.

15. A method according to claim 13, wherein the transgene comprises cre recombinase, the tumour suppressor function results from a tumour suppressor gene, and the tumour suppressor gene, or a functional part thereof, is flanked with loxp sites.

16. A method according to claim 13, wherein a product of the transgene comprises an antisense RNA or ribozyme RNA which is capable of inhibiting expression of a tumour suppressor gene.

17. A method according to claim 12, wherein the tumour suppressor gene comprises p53.

18. A method according to claim 8, wherein the oncogene comprises myc, abl, bcl-2, v-rel, ras, papillomavirus E6 protein, papillomavirus E7 protein, adenovirus EIA, PIM1, RhoH/TTF or PAX5.

19. A method according to claim 1, wherein the transgenic mouse comprises antibody-secreting cells in which a tumour suppressor gene has been deleted.

20. A method according to claim 1, wherein the method comprises the further step of immunising the transgenic mouse with an antigen before step (b).

21. A method according to claim 20, further comprising selecting an antibody-secreting cell which produces an antibody which recognises the antigen.

22. A method according to claim 3, wherein step (d) comprises fluorescence activated cell sorting.

23. A method according to claim 1, wherein the transgenic mouse is not immunised.

24. A method according to claim 1, wherein the stimulus comprises a temperature change.

25. A method according to claim 1, wherein the stimulus comprises a chemical stimulus.

26. A method according to claim 1, wherein the antibody-secreting cells are B lymphocytes.

27. A method according to claim 1, wherein the antibody is a humanised antibody.

28. A method according to claim 1, comprising a further step of storing the antibody-secreting cells at a temperature of 0° C. or below, after extracting the antibody-secreting cells from the mouse, and before or after exposing the antibody-secreting cells to the stimulus.

29. A method for producing a monoclonal antibody, comprising producing a population of immortalised cells by a method as defined in claim 3, and producing the monoclonal antibody from the population of immortalised cells.

30. A method according to claim 13, wherein the tumor suppressor function comprises p53.

31. A method for producing antibodies comprising:
(a) providing a germline transgenic mouse having antibody-secreting cells capable of expressing one or more transgenes, wherein the antibody-secreting cells are in a non-immortalised state in the absence of a stimulus and change to an immortalised state by means of the transgene or transgenes upon exposure of the cells to the stimulus;
(b) extracting the antibody-secreting cells from the mouse;
(c) exposing the antibody-secreting cells to the stimulus, thereby immortalising the antibody-secreting cells by means of the transgene or transgenes; and
(d) collecting antibodies from the antibody-secreting cells, wherein the antibody-secreting cells are B lymphocytes.

32. A method for producing antibodies comprising:
(a) providing a germline transgenic mouse having antibody-secreting cells capable of expressing one or more transgenes, wherein the antibody-secreting cells are in a non-immortalised state in the absence of a stimulus and change to an immortalised state by means of the transgene or transgenes upon exposure of the cells to the stimulus, which mouse has been immunised with an antigen;
(b) extracting the antibody-secreting cells from the mouse;
(c) exposing the antibody-secreting cells to the stimulus, thereby immortalising the antibody-secreting cells by means of the transgene or transgenes; and
(d) collecting antibodies from the antibody-secreting cells.

* * * * *